United States Patent [19]
Chen et al.

[11] Patent Number: 6,018,033
[45] Date of Patent: Jan. 25, 2000

[54] HYDROPHILIC, HYDROPHOBIC, AND THERMOREVERSIBLE SACCHARIDE GELS AND FORMS, AND METHODS FOR PRODUCING SAME

[75] Inventors: Jun Chen, Hatfield, Pa.; Seong BongJo; Kinam Park, both of West Lafayette, Ind.

[73] Assignee: Purdue Research Foundation, West Lafayette, Ind.

[21] Appl. No.: 08/855,588

[22] Filed: May 13, 1997

[51] Int. Cl.$^7$ .......................... C07H 15/10; C07H 15/04; C07H 15/12

[52] U.S. Cl. .......................... 536/4.1; 536/17.2; 536/17.3; 536/17.9; 536/18.2; 536/18.5; 536/55.3; 536/103; 536/123.1; 536/123.13; 424/1.1; 424/456; 424/461; 424/466

[58] Field of Search .............................. 536/55.3, 123.1, 536/4.1, 17.2, 17.3, 17.9, 18.2, 18.5, 103, 123.13; 424/1.1, 456, 461, 466

[56] References Cited

U.S. PATENT DOCUMENTS

| | | |
|---|---|---|
| 3,103,508 | 9/1963 | Fisher et al. . |
| 3,215,137 | 11/1965 | Laakso . |
| 3,225,012 | 12/1965 | Black et al. . |
| 3,356,652 | 12/1967 | Ray-Chaudhuri . |
| 4,042,538 | 8/1977 | Lucas . |
| 4,663,388 | 5/1987 | Douglass et al. . |
| 5,116,961 | 5/1992 | Sachinvala . |
| 5,149,335 | 9/1992 | Kellenberger et al. . |
| 5,164,492 | 11/1992 | Kitazawa et al. . |
| 5,173,554 | 12/1992 | Kitazawa et al. . |
| 5,248,747 | 9/1993 | Sachinvala et al. . |
| 5,580,940 | 12/1996 | Oosterhoff . |
| 5,693,768 | 12/1997 | Bachmann et al. ...................... 536/4.1 |

FOREIGN PATENT DOCUMENTS

| | | |
|---|---|---|
| 0 374 752 | 6/1990 | European Pat. Off. . |
| 0 668 294 | 8/1995 | European Pat. Off. . |
| 2 679 566 | 1/1993 | France . |
| WO 94/14823 | 7/1994 | WIPO . |

OTHER PUBLICATIONS

Gruber, H. Hydrophile polymergele mit reaktiven gruppen, I. Herstellung und polymerisation von glucose–und saccharosemethacrylaten; *Monatsch. F. Chem.*, 1981, 112, 273.

Patil, D.R.; Rethwisch, D.R.; Dordick, J.S.; Enzymatic synthesis of a sucrose–containing linear polyester in nearly anhydrous organic media; *Biotechnology and Bioengineering*, 1991, 37, 639.

Garcia–Gonzalez; Kellaway, I.W.; Blanco–Fuente, H.; Anguiano–Igea, S.; Delgado–Charro, B; Otero–Espinar, F.J.; Blanco–Mendez, J; Design and evaluation of buccoadhesive metoclopramide hydrogels composed of poly(acrylic acid) crosslinked with sucrose; *Int'l. J. Pharm.*, 1993, 100, 65.

Lepisto, M.; Artursson, P.; Edman, P.; Laakso, T.; Sjoholm, L.; Determination of the degree of derivatization of acryloylated polysaccharides by fourier transform proton NMR spectroscopy; *Anal. Biochem.*, 1983, 133, 123.

Laakso, T.; Stjarnkvist, P.; Sjoholm, I.; Biodegradable microspheres VI: Lysosomal release of covalently bound antiparasitic drugs from starch microparticles; *J. Pharm. Sci.*, 1987, 76, 134.

Artursson, P; Edman, P; Laakso T.; Sjoholm, I.; Characterization of polyacryl starch microparticles as carriers for proteins and drugs; *J. Pharm. Sci.*, 1984, 73, 1507.

Edman, P.; Ekman, B; Sjoholm, I; Immobilization of proteins in microspheres of biodegradable polyacryldextrans; *J. Pharm. Sci.*, 1980, 69, 838.

Sachinvala, N.D., Ju. R.F., Litt, M.H., and Niemczura, W.P., Preparation of poly(methyl methacrylate) and copolymers having enhanced thermal stabilities using sucrose–based comonomers and additives., *Journal of Polymer Science: Part A: Polymer Chemistry*, 1995, 15–29.

Smedt, S.C.D.; Lauwers, A.; Demeester, J.; Steenbergen, M.J.V.; Hennink, W.E.; Foefs S.P.F.M.; Characterization of the network structure of dextran glycidyl methacrylate hydrogels by studying the rheological and swelling behavior; *Macromolecules*, 1995, 28, 5082.

Park, K.; Enzyme–digestible swelling hydrogels as platforms for long–term oral drug delivery: Synthesis and characterization; *Biomaterials*, 1988, 9, 435.

Shalaby, W.S.W.,; Park, K.; Biochemical and mechanical characterization of enzyme–digestible hydrogels; *Pharmaceutical Research*, 1990, 7, 816.

Starks, C.M.; Phase transfer catalysis. I. Heterogeneous reaction involving anion transfer by quaternary ammonium and phosphonium salts; *JACS*, 1971, 93, 195.

Hoppe, H.; Koppe, J.; Winkler, F.; Improved method for determining acrylamide in polyacrylamide; *Plaste Kautsch*, 1977, 24, 105.

Akoh, C.C.; Swanson, B.G.; One–stage synthesis of raffinoise fatty acid polyesters; *J. Food Sci.*, 1987, 52, 1570.

Akoh, D.C.; Swanson, B.G.; Synthesis and properties of alkyl glycoside and starchyose fatty acid polyesters; *J. Am. Oil Chem. Soc.*, 1989, 66, 1295.

(List continued on next page.)

*Primary Examiner*—James O. Wilson
*Attorney, Agent, or Firm*—McDermott, Will & Emery

[57] ABSTRACT

Polymerizable saccharide monomers are made by the reaction of a saccharose and a (meth)acrylate. Hydrophilic, hydrophobic and thermoreversible gels and foams are formed upon polymerization of the saccharide monomers. Hydrophilic sucrose monomers are synthesized by reaction of sucrose with an epoxy acrylate. Hydrophobic sucrose monomers are synthesized by reaction of sucrose with methacrylol chloride followed by acetyl chloride. Thermoreversible sucrose monomers are obtained by modifying sucrose with polymerizable substituents prepared from methacryloyl chloride and aminocarboxylic acids. The modified sucrose monomers are copolymerized with hydrophobic poly(alkyleneoxide) (meth)acrylates to produce hydrogels exhibiting inverse thermoreversible properties. The thermosensitive hydrogels are biodegradable and can be used in the area of controlled drug delivery.

41 Claims, 14 Drawing Sheets

OTHER PUBLICATIONS

Wehrli, F.W. and Wirthlin, T. *Interpretation of C–13 NMR spectra*, Heyden and Sons Inc.; New York, NY, 1976, 225.

Shalaby, W.S.W.; Blevins, W.E.; Park, K.; In vitro and in vivo studies of enzyme–digestible hydrogels for oral drug delivery; *Journal of Controlled Release*, 1992, 19, 131.

Huglin, M; Zakaria, M., Observations of the homogeneity of crosslinked copolymers prepared by y–irradiation; *Polymer*, 1984, 25, 797.

Davis, T; Huglin, M.; Some mechanical properties of poly(2–hydroxyethyl methacrylate) gels swollen in water/1, 4–dioxane mixtures; *Makromol Chem. Rapid Commun.*, 1988, 9, 39.

Garcia, O; Trigo, R.M.; Blanco, M.D.; Teijon, J.M.; Influence of degree of crosslinking on 5–fluorouracil release from poly(2–hydroxyethyl methacrylate) hydrogels; *Biomaterials*, 1994, 15, 689.

Jin, X.; Carfagna, C; Nicolais, L.; Lanzetta. R.; Synthesis, characterization, and in vitro degradation of a novel thermotropic ternary copolyester based on p–hydroxybenzoic acid, glycolic acid, and p–hydroxycinnamic acid; *Macromolecules*, 1995, 28, 4785.

Dubrovskii, S.A.; Afaneseva, M.V.; Lagutina, M.A.; Kazanskii, K.S.; Measurement of swelling in weakly crosslinked hydrogels; *Polymer Science U.S.S.R.*, 1990, 32, 166.

Hartley, F.D.; Cross, M.M.; Lord, F.W.; The mechanism of polyurethane foam formation; In *Advances in Polyurethane Technology*; J. M. Buist and H. Gudgeon, Eds,; John Wiley and Sons Inc.; New York, NY, 1968, 139.

Tomlinson, E.; Burger, J.J.; Incorporation of water–soluble drugs in albumin microspheres; In *Methods in Enzymology*; K. J. Widder and R. Green, Eds.; Academic press, Inc.; 1985, 112, 35.

Straathof, A.J.J.; Vrijenhoef, J.P.; Sprangers, E.P.A.T.; Bekkum, H.V.; Kieboom, A.P.G.; Enzymic formation of β–D–fructofuranosides from sucrose: activity and selectivity of invertase in mixtures of water and alcohol; *J. Carbohydrate Chemistry*, 1988, 7, 223.

Hickmott, P.W.; Reaction of αβ–unsaturated acid chlorides with alcohols in the presence of tertiary amines; *J. Chem. Soc.*, 1964, 883.

Strumia, M.C.; Zamora, M.N.; Bertorello, H.E.; Hydrogels from acrylic sucrose. Synthesis and characterization; *J. Appl. Poly. Sci.*, Applied Polymer Symposium 49, 9–14, 1991.

Jeong, S.Y.; Kim, S.W.; Eenink, M. J. D.; Feijen, J. Self-–regulating insulin delivery systems. I. Synthesis and characterization of glycosylated insulin; *J. Cont. Rel.*, 1984,1, 57.

Horbett, T.A.; Ratner, B.D.; Kost, J.; Singh, M. *A bioresponsive membrane for insulin delivery*; Plenum Press: New York, 1984, 209.

Yoshida, R.; Sakai, K.; Okano, T.; Sakurai, Y. Pulsatile drug delivery systems using hydrogels; *Adv. Drug Delivery Reviews*, 1993, 11, 85.

Hoffman, A.S.; Afrassiabi, A. and Dong, L.C., Thermally reversible hydrogels: II. Delivery and selective removal of substances from aqueous solutions., *J. Cont. Rel.*, 1986, 4, 213–222.

Dong, L.C. and Hoffman, A.S., Thermally reversible hydrogels: III. Immobilization of enzymes for feedback reaction control, *J. Cont. Rel.*, 1986, 4, 223–227.

Shalaby, S. W. Thermoreversible gels; In *Water–solution polymers; Synthesis, solution properties, and applications*; S.W. Shalaby, C.L. McCormick and G.B. Butler, Eds.; American Chemical Society; Washington D.C., 1991, 467, 502.

Bae, Y.H., Okano, T. and Kim, S.W., *Makromolek. Chem., Rapid Commun.*, (1988) 9, 185.

Yoshida, M., Asano, M. and Kumakura, M., A new temperature–sensitve hydrogel with α–amino acid group as side chain of polymer., *Eur. Polym. J.*, (1989) 25, 1197–1202.

Yoshida, M., Suzuki, Y., Tamada, M., Kumakura, M. and Katakai, R., External stimulus–responsive poly(methacryloyldipeptides) having sequences of L–amino acyl–L–alanine ethyl esters as pendent groups., *Eur. Polym. J.* (1991) 27, 493–499.

Bae, Y.H., Okano, T., Hsu, R. and Kim, S.W., *Makromolek. Chem., Rapid Commun.*, (1987) 8, 481.

Patil, D.R., Rethwisch, D.G., and Dordick, J.S., Enzymatic synthesis of a sucrose–containing linear polyester in nearly anhydrous organic media., *Biotechnology and Bioengineering*, 1991, 639–646.

Kulkarni, R.K. and Morawetz., H., Effect of asymmetric centers on free radical polymerization and the properties of polymers: methacrylyl alanine, methacrylyl glutamic acid, acrylyl glutamic acid and their polymers., *J. Polym. Sci.*, (1961) 54, 491–503.

Kaczmar, B.U. and Traser, S., Schlangenkafig–Polymere, 1. Darstellung verschiedener Schlangenkafig–polyelektrolyte auf der Basis von Polyacrylamiden und einem Anionenaustauscher., *Makromol. Chem.*, (1976) 177, 1981–1989.

Yeoh, K.W., Chew, C.H., Gan, L.M. and Koh, L.L., Synthesis and polymerization of surface–active sodium acrylamidoundecanoate., *J. Macromol. Sci.–Chem.*, (1989) A26, 663–680.

Abouhilale, S., Greiner, J. and Riess, J.G., One–step preparation of 6–perfluoroalkylalkanoates of trehalose and sucrose for biomedical uses., *Carbohydrate Research* (1991) 212, 55–64.

Jansson, P.–E., Kenne, L. and Schweda, E., Nuclear magnetic resonance and conformational studies on monoacetylated methyl D–gluco– and D–galacto–pyranosides., *J. Chem. Soc. Perkin Trans.*, (1987) 1, 377–383.

Modrzejewski, F. and Wochna L., Investigation of the swelling power of tablet disintegrants., *Acta Poloniae Pharmaceutica*, (1965) 396–402.

Wehrli, F.W., Marchand, A.P., and Wehrli S., *Interpretation of carbon–13 NMR spectra*, (1988).

Lindblom, L. and Elander, M., Phase–transfer catalysis in the production of pharmaceuticals., *Pharmaceutical Technology*, (1980) 56–69.

Bae, Y.H., Okano, T., and Kim S.W., On–Off Thermocontrol of solute transport. I. Temperature dependence of swelling of N–Isopropylacrylamide networks modified with hydrophobic components in water., *Pharmaceutical Research*, (1991) 531–537.

Okano, T., Bae, Y.H., Jacobs, H., and Kim, S.W., Thermally on–off switching polymers for drug permeation and release., *Journal of Controlled Release*, (1990) 255–265.

Berjano, M., Guerrero, A., Muñoz, J., and Gallegos, C., Temperature dependence of viscosity for sucrose laurate/water micellar systems., *Collid & Polymer Science* (1993) 600–606.

Alvarex, C., Bertorello, H., and Strumia, M., Application of poly (butadience–co–acrylic acid) –Sucrose as gel in the separation of different substances., *Journal of Applied Polymer Science*, (1992) 25–27.

Alvarez, C., Bertorello, H., and Strumia, M., Retention of heavy metal ions by a new synthetic hydrogel., *Polymer Communications*, (1991) 504–505.

Augusta, S., Gruber, H.F., and Streichsbier, F., Synthesis and antibacterial activity of immobilized quarternary ammonium salts., *Journal of Applied Polymer Science*, (1994) 1149–1163.

; X = Cl, Br
Y = Cl, Br

; X = Cl, Br

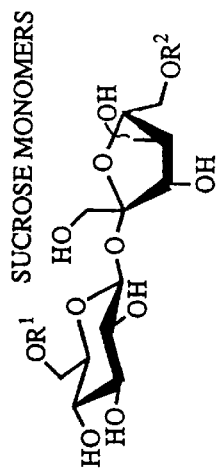

Figure 7(A) SUCROSE MONOMERS

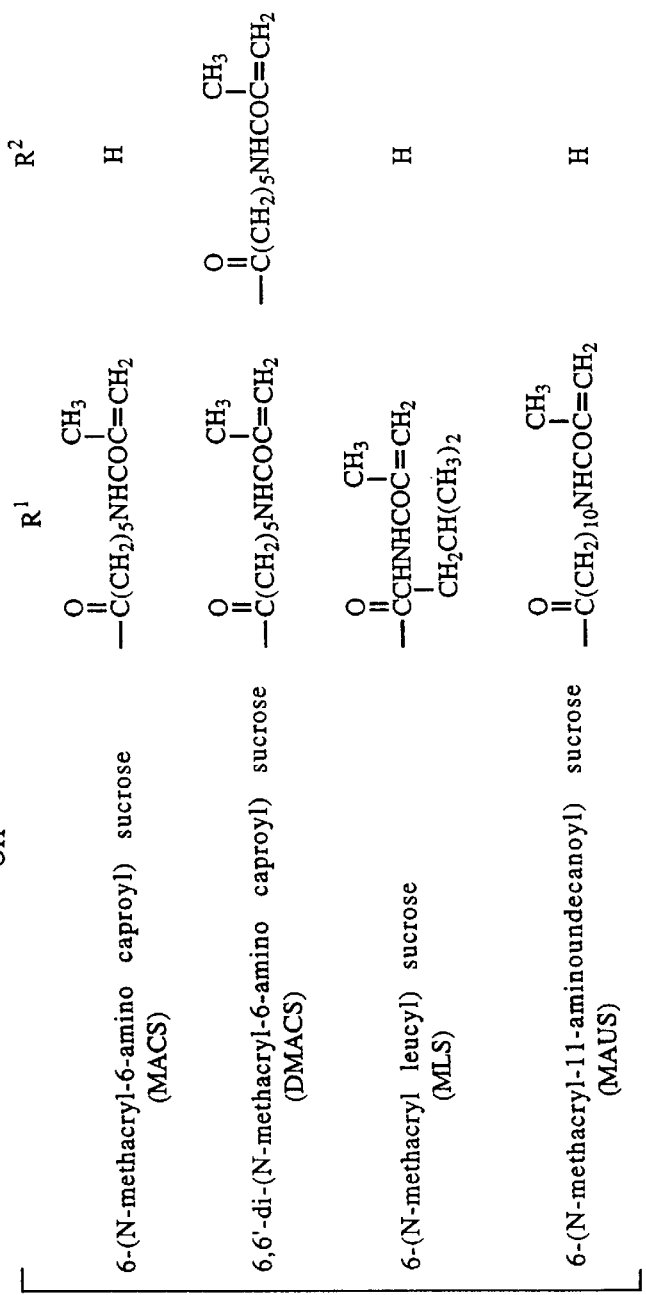

Figure 7(B)

| | $R^1$ | $R^2$ |
|---|---|---|
| 6-(N-methacryl-6-amino caproyl) sucrose (MACS) | $-\overset{O}{\overset{\|}{C}}(CH_2)_5NHCOC(CH_3)=CH_2$ | H |
| 6,6'-di-(N-methacryl-6-amino caproyl) sucrose (DMACS) | $-\overset{O}{\overset{\|}{C}}(CH_2)_5NHCOC(CH_3)=CH_2$ | $-\overset{O}{\overset{\|}{C}}(CH_2)_5NHCOC(CH_3)=CH_2$ |
| 6-(N-methacryl leucyl) sucrose (MLS) | $-\overset{O}{\overset{\|}{C}}CHNHCOC(CH_3)=CH_2$ <br> $\quad\ \ \|$ <br> $\quad CH_2CH(CH_3)_2$ | H |
| 6-(N-methacryl-11-aminoundecanoyl) sucrose (MAUS) | $-\overset{O}{\overset{\|}{C}}(CH_2)_{10}NHCOC(CH_3)=CH_2$ | H |

HYDROPHOBIC MONOMERS

Figure 7(C)

Poly(propylene glycol) methacrylate (PPGM): $H_2C=C(CH_3)CO_2(CH_2CH(CH_3)O)_n\text{-}H$ Poly(ethylene glycol) ethylether methacrylate (PEGEEM): $H_2C=C(CH_3)CO_2(CH_2CH_2O)_n\text{-}CH_2CH_3$

HYDROPHILIC, HYDROPHOBIC, AND THERMOREVERSIBLE SACCHARIDE GELS AND FORMS, AND METHODS FOR PRODUCING SAME

TECHNICAL FIELD

The present invention relates to gels and foams derived from saccharides. The invention particularly relates to polymerizable derivatives of saccharides, e.g., sucrose. The gels and foams can be used in the controlled release of drugs.

BACKGROUND OF THE INVENTION

Saccharides are ubiquitously present in plants and some are quite inexpensive. Even highly purified sucrose can be obtained at low cost. All of the hydroxyl groups of a saccharide molecule can be chemically modified, e.g., the eight hydroxyl groups of sucrose. The degree of modification can be controlled, for instance, by changing the reaction ratio. These considerations have led to extensive research on the chemistry of the saccharides, particularly the least expensive ones.

For example, the research literature reveals that sucrose has been used to build polymer networks [Gruber, H. (1981); Patil, D., et al., (1991); Garcia-Gonzalez, et al., (1993)]. Glycidyl (meth)acrylates have been used to modify polysaccharides, such as starch [Lepisto, M., et al. (1983); Laakso, T., et al., (1987); Artursson, P., et al. (1984)] and dextran [Edman, P., et al. (1980); Smedt, S. C. D., et al. (1995)]. Also, the formation of swellable hydrogels from proteins, such as albumin, has been described [Park, K., (1988); Shalaby, W. S. W., et al. (1990)]. Polymer hydrogels and microspheres have been made by these approaches.

Hydrophilic gels have been prepared from sucrose, for example, by polymerization of a sucrose ester. Thus, polymerization of a sucrose acrylate monomer has been described [Strumia, M. C., et al. (1991)]. Further, linear polyesters of sucrose have been described [Patil et al., (1991)]. These latter sucrose linear polyesters were produced using an enzyme system.

Although extensive research has been performed on hydrogels, little research is related to hydrogel foams. When the hydrogel foams are formed, the polymer chains are separated by empty spaces. Thus, water can be absorbed into the foams by capillary reaction. Furthermore, the porous structure affords foams having hundreds of times more surface area and shorter diffusion distance than hydrogels, making the swelling rate of foams hundreds of times faster than that of hydrogels. The fast swelling ability is important, for instance, in designing controlled release drug delivery systems, especially oral dosage forms [Shalaby, W. S. W., et al. (1992)].

Additionally, environment-sensitive hydrogels have been studied extensively. Hydrogels having the ability to respond to changes in environmental factors such as pH, temperature, electric field, or light can find application in drug delivery, biotechnology, biosensors, and semiconductors. Moreover, hydrogels that can respond to stimuli caused by particular diseases may provide a basis for developing new smart drug delivery systems. For example, attempts have been made to develop hydrogel systems that respond to pH changes and specific ligands in delivering insulin, however, they are unsatisfactory. [Jeong, S. Y., et al., (1984); Horbett, T. A., et al. (1984)].

Thermoreversible hydrogels have been proposed for use in a new drug delivery system as well as a bioseparation system [Yoshida, R., et al., (1993); Hoffman, A. S., et al., (1986); Dong, L. C., et al., (1986)]. Various applications for thermoreversible hydrogel systems have been proposed by researchers [Shalaby, S. W. (1991)].

Thermoreversible hydrogels prepared by the copolymerization of N-isopropyl acrylamide and methacrylic acid, lightly crosslinked with N,N-methylene-bisacrylamide have been studied [Hoffman, A. S., et al., (1986); Dong, L. C., et al., (1986)]. Copolymer hydrogels of N-isopropyl acrylamide and butyl methacrylate reportedly exhibited thermoreversible changes in volume with temperature [Bae, Y. H., et al., (1988)]. Also, hydrogels containing N-methacryloyl α-amino acid esters and 2-hydroxypropyl methacrylate, which were crosslinked with polyethylene glycol (600) dimethacrylate, were reported to show temperature-dependent reversible volume changes [Yoshida, M., et al., (1989)]. Hydrogels synthesized from methacryloyl dipeptides have also been characterized [Yoshida, M., et al., (1991)]. In addition, an interpenetrating polymer network of N-acryloyl pyrrolidone and poly(oxyethylene) has been described [Bae, Y. H., et al. (1987)].

In the patent art, U.S. Pat. No. 3,103,508 discloses polymerizable esters formed from sugars and α,β-unsaturated polymerizable acids.

U.S. Pat. No. 3,215,137 discloses an immobilizing bandage which employs a sucrose ester, the viscosity of which may be reduced by addition of a polyethylene glycol dimethacrylate.

U.S. Pat. No. 3,225,012 discloses nylon-type polyamides derived from carbohydrates.

U.S. Pat. No. 3,356,652 discloses vinyl derivatives of tetra-acetylated glucose.

U.S. Pat. No. 4,042,538 discloses vinylbenzoyl esters of mono- and disaccharides, which can be copolymerized with styrene or methacrylates.

U.S. Pat. No. 4,663,388 discloses a "coupling agent", which comprises a saccharide having a pendant ethylenically unsaturated group, such as an acrylamide moiety.

U.S. Pat. No. 5,164,492 relates to approaches to forming polymers having saccharide residues at their sidechains.

U.S. Pat. No. 5,116,961 discloses the formation of a trimethacryloyl sucrose having methylated hydroxyl groups. U.S. Pat. No. 5,248,747, which is a continuation-in-part of U.S. Pat. No. 5,116,961, relates to polymers formed using the trimethacryloyl sucrose as a cross-linking agent.

Desired are novel saccharide monomers that can be polymerized to form biodegradable gels and foams. Such gels and foams should be more environmentally friendly than purely synthetic gels and foams, and may be imparted with physical and chemical properties conducive to their use in medical and veterinary applications.

SUMMARY OF THE INVENTION

The present invention is for novel unsaturated saccharide compounds that are polymerizable to form gels and foams. These saccharide compounds are represented hereinbelow by formulas (I–VII) as follows:

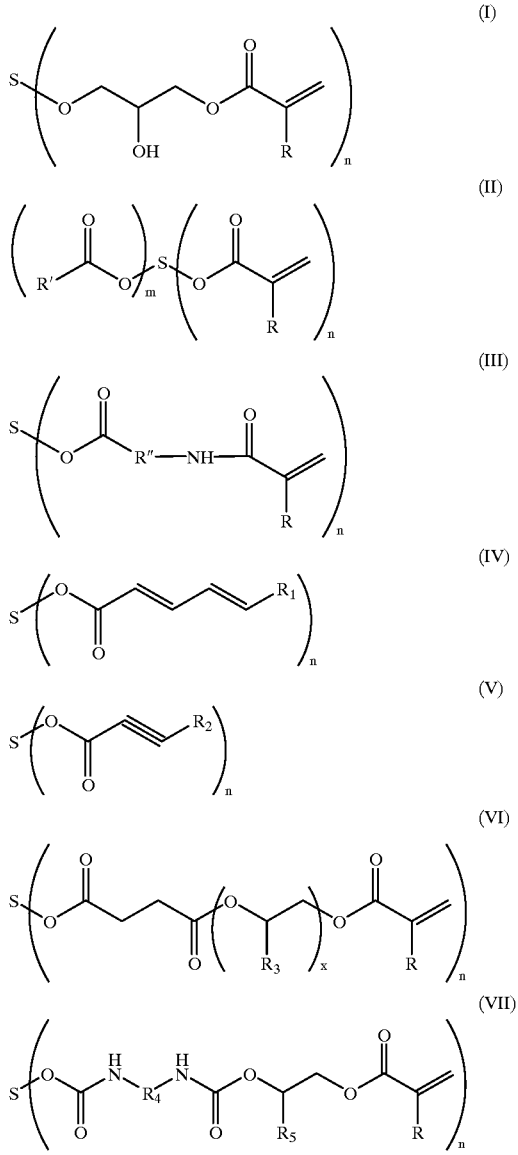

In each of the above formulas, S represents a saccharide residue, R is hydrogen or a lower alkyl group, e.g., methyl, and n is an integer from 1 to 8. In formula (II), R' represents an alkyl, aryl or alkaryl group, and m is an integer from 0 to 7. In formula (III), R" represents an alkylene, arylene or alkarylene diradical. In formula (IV), $R_1$ represents a lower alkyl group. In formula (V), $R_2$ represents a lower alkyl group. In formula (VI), $R_3$ is hydrogen or methyl, and x is an integer from 1 to 10,000. In formula (VII), $R_4$ represents a diradical, which can be an alkylene chain, and aromatic group, or an alkaryl group, and $R_5$ represents hydrogen or a lower alkyl group.

A hydrophilic saccharide gel is formed by polymerizing a saccharide monomer having formula (I) above. A hydrophobic gel is formed by polymerizing a saccharide monomer having formula (II) above. A gel having inverse thermoreversible properties is formed by copolymerizing a saccharide monomer having formula (III) above with a poly(alkyleneoxide) (meth)acrylate monomer, as defined herein, with or without a crosslinking agent.

Polymerization of a saccharide monomer having formula (IV) or (V) above produces a hydrophobic saccharide gel. Whenever a saccharide monomer having formula (VI) or (VII) is polymerized, a hydrophilic gel is produced.

Foams can also be produced by polymerizing a saccharide monomer shown above in formulas (I–VII), in the presence of a blowing agent. Particularly preferred are foams that have been dehydrated with an organic solvent, such as ethanol or acetone. Such foams have hydrophilic, hydrophobic or inverse thermoreversible properties, respectively.

Preferred saccharides include mono-, di-, tri- and higher oligosaccharides. More preferably a disaccharide is employed, most preferably, sucrose.

Associated methods of forming the instant saccharide monomers and polymers from a saccharide and corresponding (meth)acrylate are contemplated.

BRIEF DESCRIPTION OF THE DRAWINGS

FIG. 7 illustrates the structures of monomers used in the preparation of thermoreversible sucrogels of the present invention.

DETAILED DESCRIPTION OF THE INVENTION

Figure 1A:
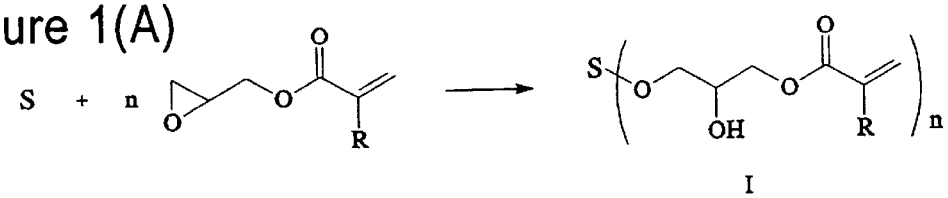
FIG. 1 illustrates chemical reactions that are the subject of the present invention, wherein S represents a saccharose.

A vinyl-type (or acetylenic-type) saccharide monomer of the present invention is represented by formulas (I–VII) hereinbelow:

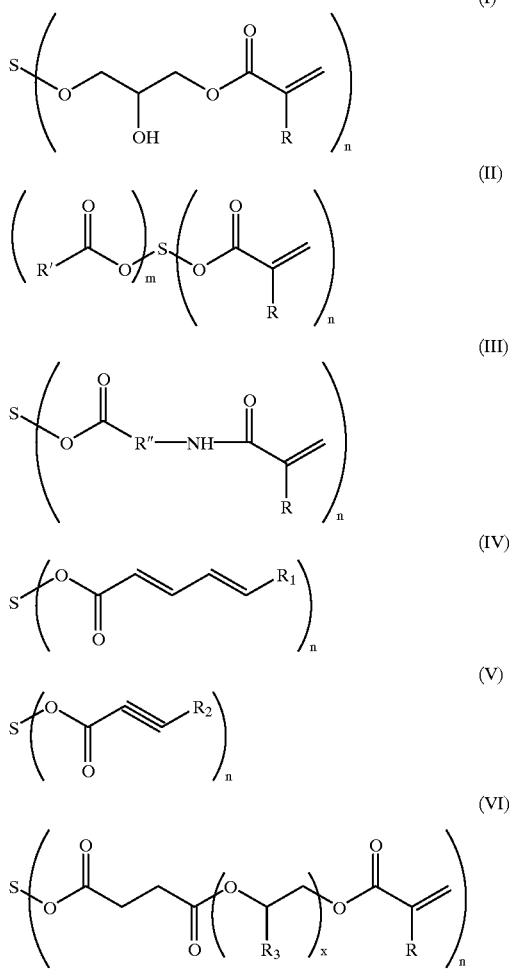

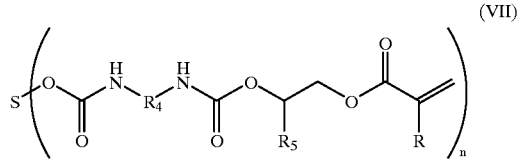

In formulas (I–VII), S represents a saccharide residue. The R group in each of the formulas can be hydrogen or a lower alkyl group. A preferred lower alkyl group is methyl. Accordingly, a (meth)acrylate moiety is preferred. In formulas (I–VII), n is an integer from 1 to 8, and represents the extent of modification of the saccharide residue, e.g., with a (meth)acrylate group.

In formula (II), m is an integer from 0 to 7, and represents the extent to which the saccharide residue is modified with a hydrophobic group. The R' group in formula (II) can be an alkyl group, an aryl group, or an alkaryl group. When R' is an alkyl group, it is most preferably a lower alkyl group, e.g., methyl. A preferred aryl group is phenyl. A preferred alkaryl group is benzyl.

In formula (III), the R" group is an alkylene, arylene, or alkarylene diradical. Preferably, R" is a straight or branched chain alkylene group. For example, the R" group in formula (III) can be a methylene chain having the formula $(CH_2)_p$, where p represents the repeat number of methylene units, and ranges from 1 to 40, preferably 1 to 20, most preferably 4 to 12.

In formula (IV), the terminal $R_1$ group is preferably a lower alkyl group. The conjugated diene structure of the monomer can be polymerized in the usual free radical manner, i.e., with one or both olefin groups being saturated upon polymerization. Alternatively, the diene can react with an olefin of another molecule in Diels-Alder fashion, with the remaining unreacted olefin group being polymerized.

The terminal $R_2$ group of formula (V) is preferably a lower alkyl group. The alkynyl functionality of the molecule can be polymerized in free radical fashion, either once to produce an alkenyl functionality, or twice to saturate the molecule.

In formula (VI), a repeating glycol group is present in the molecule and is an ethylene oxide or propylene oxide group, i.e., $R_3$ represents a hydrogen or methyl group. In the formula, x represents the repeat number of the glycol group, and is an integer from 1 to 10,000. Adjacent to the saccharose group of the molecule is an opened-up succinic anhydride linkage, which couples the glycol-(meth)acrylate portion of the molecule to the saccharose.

In formula (VII), $R_4$ represents a hydrocarbon diradical, i.e., an alkylene chain, aromatic group, or alkaryl group. Preferred groups for $R_4$ are n-butenyl, n-hexenyl, and n-octenyl chains, and among arylene and aralkylene groups, a tolyl diradical is preferred. $R_5$ of the formula represents hydrogen or a lower alkyl group, e.g., methyl.

A hydrophilic saccharide gel is formed by polymerizing a saccharide monomer having formula (I) above. A hydrophobic gel is formed by polymerizing a saccharide monomer having formula (II) above. A gel having inverse thermoreversible properties is formed by copolymerizing a saccharide monomer having formula (III) above with a poly(alkyleneoxide) (meth)acrylate monomer, as defined herein, with or without a crosslinking agent.

Polymerization of a saccharide monomer having formula (IV) or (V) above produces a hydrophobic saccharide gel.

Whenever a saccharide monomer having formula (VI) or (VII) is polymerized, a hydrophilic gel is produced.

Hydrophilic, hydrophobic and inverse thermoreversible foams can also be produced by polymerizing a saccharide monomer shown above in formulas (I–VII), respectively, in the presence of a blowing agent. Whenever such foams are dehydrated with an alcohol, e.g., ethanol, as described hereinbelow, particularly desirable properties can be obtained.

Also contemplated are methods of synthesizing the unsaturated saccharide monomers defined by formulas (I–VII) hereinabove. The reactions are illustrated in FIG. 1.

Thus, as shown in FIG. 1A, a method for forming a saccharide monomer defined by formula (I) entails reacting the saccharide with an epoxy (meth)acrylate, such as glycidyl (meth)acrylate.

Figure 1B:
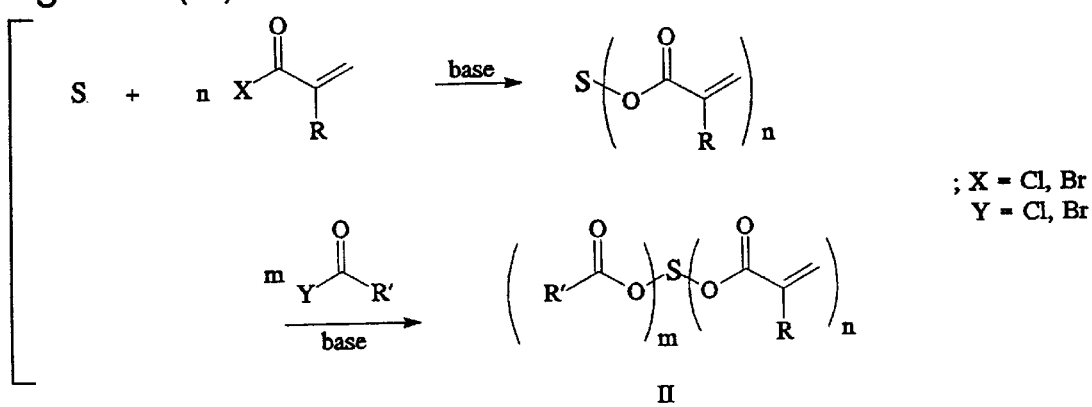

As shown in FIG. 1B, a method of synthesizing an ethylenically-unsaturated saccharide monomer according to formula (II) comprises reacting a saccharose with a (meth) acrylohalide in the presence of a base to form a saccharide (meth)acrylate. The saccharide (meth)acrylate is then reacted with an acyl halide in the presence of a base to form the ethylenically-unsaturated saccharide monomer. The halide leaving group in both instances can be chloride or bromide. A preferred (meth)acrylohalide is methacrylochloride, and an exemplary acyl halide is acetyl chloride.

Figure 1C:
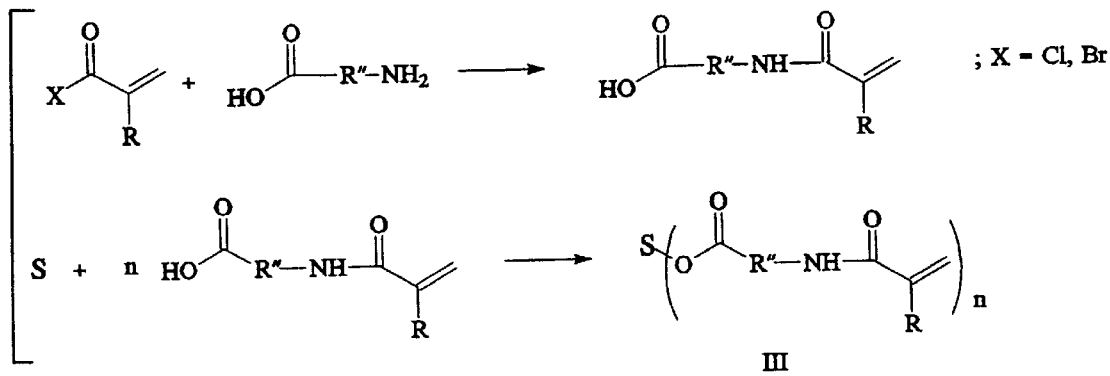

As shown in FIG. 1C, a method of forming an ethylenically-unsaturated saccharide monomer according to formula (III) comprises reacting a saccharose with a (meth) acryloyl aminocarboxylic acid. The (meth)acryloyl aminocarboxylic acid is represented by the following formula:

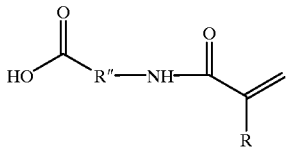

In the formula for the (meth)acryloyl aminocarboxylic acid, R represents hydrogen or a lower alkyl group and R" represents an alkylene, arylene, or alkarylene diradical, preferably a straight or branched chain alkylene group. Whenever the R" group in the formula is a simple methylene chain represented by the formula $(CH_2)_p$, p ranges from 1 to 40, preferably 1 to 20, and most preferably 4 to 12.

A reaction scheme for forming the (meth)acryloyl aminocarboxylic acid is depicted in FIG. 1C. Particularly preferred (meth)acryloyl aminocarboxylic acids are N-methacryl-6-aminocaproic acid, N-methacryl-leucine, and N-methacryl-11-aminoundecanoic acid, the formulas of which appear in FIG. 7.

Figure 1D:
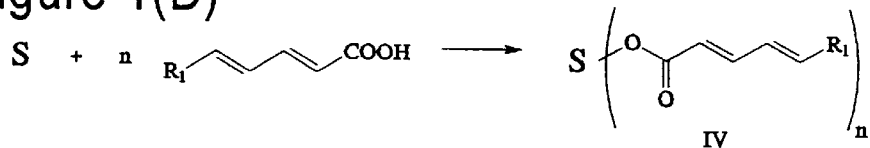
Figure 1E:

As shown in FIG. 1D, a method of forming the dienyl saccharide of formula (IV) is depicted. Accordingly, a 2,4-dienyl carboxylic acid is reacted with hydroxyl groups of the saccharide to form an ester linkage. Similarly, as shown in FIG. 1E, the carboxyl group of an α-alkynyl carboxylic acid is reacted with a saccharose to produce an ester thereof. Standard esterification reaction conditions can be employed.

Figure 1F:
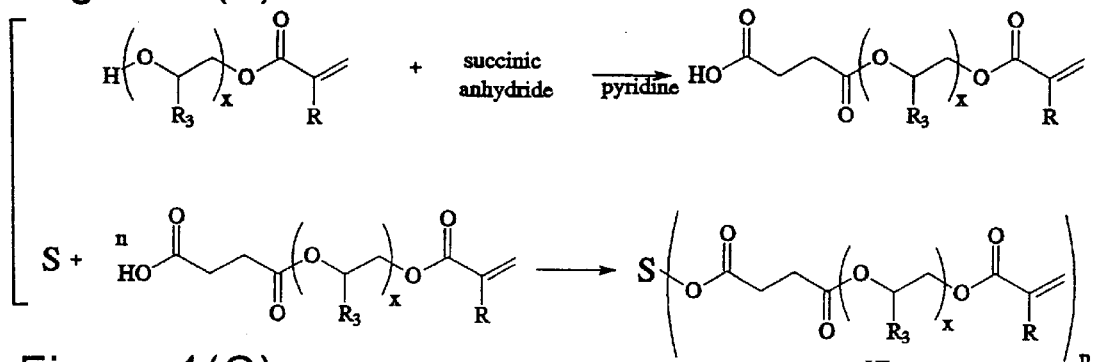

FIG. 1F depicts formation of a compound having formula (VI). Thus, a (meth)acrylate of a poly(alkylene oxide) is reacted with succinic anhydride in the presence of base to open up the anhydride ring and couple the molecule to the free alcohol group of the poly(alkylene oxide). This activated (meth)acrylate compound is then reacted with a saccharose under conventional conditions to produce an ester linkage, as represented by formula (VI).

Figure 1G:
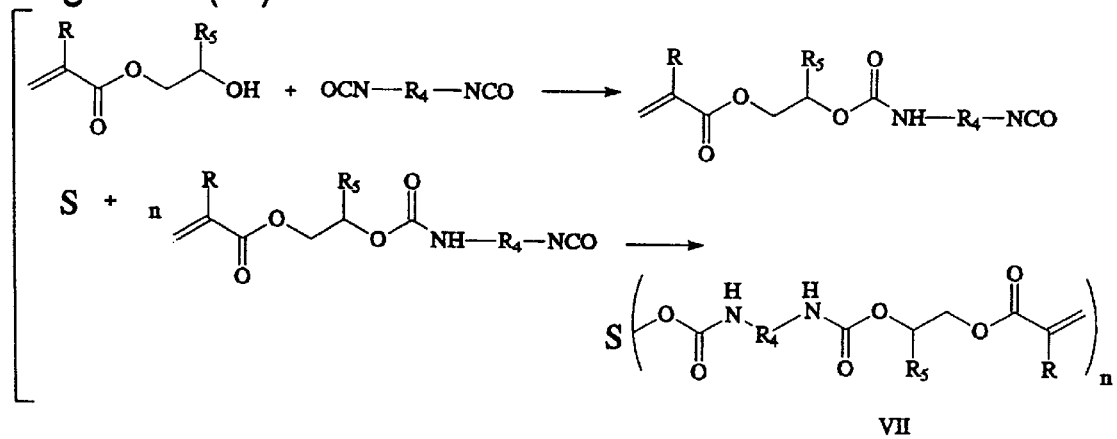

As shown in FIG. 1G, a saccharide-urethane compound as represented by formula (VII) can be produced by stoichiometrically reacting a (meth)acrylate having a terminal hydroxyl group with a diisocyanate to give a product having a single isocyanate moiety in the molecule. This product is then coupled to the saccharose via a urethane linkage to produce the target compound. Both urethane forming reactions can be conducted under standard conditions.

Examples of the alkylene group represented by R" in FIG. 1C and $R_4$ in FIG. 1G are straight chain or branched chain alkylene groups having 1 to about 22 carbon atoms, preferably about 1 to about 10 carbon atoms such as methylene, ethylene, propylene, isopropylene, butylene, isobutylene, pentylene, hexylene, heptylene, octylene, nonylene, decylene, nonadecylene, undecylene, dodecylene, tridecylene, tetradecylene, pentadecylene, hexadecylene, heptadecylene, octadecylene, and the like.

As used herein, the term "saccharide", "saccharose", "sugar", and the like, refers to a mono-, di-, tri-, or higher order saccharide or oligosaccharide. Representative monosaccharides include glucose, mannose, galactose, glucosamine, mannosamine, galactosamine, fructose, glyceraldehyde, erythrose, threose, ribose, arabinose, xylose, lyxose, allose, altrose, gluose, idose, talose, psicose, sorbose, and tagatose. Exemplary disaccharides include maltose, lactose, sucrose, cellobiose, trehalose, isomaltose, gentiobiose, melibiose, laminaribiose, chitobiose, xylobiose, mannobiose, sophorose, and the like. Certain tri- and higher oligosaccharides include raffinose, maltotriose, isomaltotriose, maltotetraose, maltopentaose, mannotriose, manninotriose, etc. Exemplary polysaccharides include starch, sodium starch glycolate, alginic acid, cellulose, carboxymethylcellulose, hydroxyethylcellulose, hydropropylcellulose, hydroxypropylmethylcellulose, ethylcellulose, carageenan, chitosan, chondroitin sulfate, heparin, hyaluronic acid, and pectinic acid.

As used herein, a "saccharide residue" further refers to a saccharide molecule having at least one pyranose or furanose ring. Also, at least one hydrogen atom is removed from a hydroxyl group of the isolated saccharide molecule, as when that group has been esterified.

The term "lower alkyl group" as used herein refers to a straight or branched chain alkyl group having 1 to 6 carbon atoms, such as methyl, ethyl, propyl, isopropyl, butyl, tert-butyl, isobutyl, and the like.

A "(meth)acrylate", as used herein refers to an α-vinylic carboxylate, e.g., a (meth)acrylic acid in which the acidic hydrogen atom has been replaced. Representative (meth) acrylic acids include acrylic, methacrylic, α-chloroacrylic, α-cyano acrylic, α-ethylacrylic, maleic, fumaric, itaconic, and half esters of the latter dicarboxylic acids.

The amount of (meth)acrylate used relative to saccharide in the reactions depicted in FIG. 1 is not specifically limited and is about 1 to about 10 moles, preferably about 1 to about 6 moles, per mole of saccharide.

Typically, a reaction of the present invention is conducted in aqueous solvent. However, an organic solvent can be used, particularly when synthesizing hydrophobic monomers and polymers, as long as it does not adversely affect the reaction. Examples of organic solvents which can be used with the present invention include halogenated hydrocarbons such as dichloromethane, chloroform, 1,2-dichloroethane, 1,1,1-trichloroethane, 1,1,2-trichloroethane, 1,1,2,2-tetrachloroethane, chlorobenzene and the like; aromatic hydrocarbons such as pyridine, benzene, toluene, xylene and the like; and ethers such as ethyl ether, isopropyl ether, ethyleneglycol dimethyl ether, ethyleneglycol diethyl ether, diethyleneglycol dimethyl ether, dioxane, tetrahydrofuran and the like. These solvents can be used alone or in combination with another solvent if desired.

A polymerization inhibitor can be employed in the present set of reactions and is not specifically limited. Examples of useful inhibitors are p-methoxyphenol, hydroquinone monomethyl ether, hydroquinone monoethyl ether, butylhydroxytoluene, butylcatechol, benzoquinone, nitrobenzene, cupric chloride, ferric chloride, etc. An inhibitor can be used singly or in combination with one or more other inhibitors. The amount of inhibitor used is not specifically limited, and is about 0.01 to about 2% by weight, based on (meth)acrylate.

Reaction temperatures and reaction times are not specifically limited, and can be readily determined by the skilled practitioner. For example, the reaction temperature for conducting the epoxy ring-opening reaction illustrated in FIG. 1A is in the range of about 10 to about 80° C., preferably about 20 to 50° C. The reaction time is in the range of about 15 minutes to 10 days. The reaction temperature for conducting the base-catalyzed coupling reactions illustrated in FIGS. 1B and 1C is in the range of about −10 to about 50° C., preferably about 0 to 30° C. The reaction time is in the range of about 1 hour to 1 week. The reaction temperature for conducting the esterification reactions illustrated in FIGS. 1C–1F is in the range of about −10 to about 50° C., preferably about 0 to 30° C. The reaction time is in the range of about 4 hours to 5 days. Standard carbamate-forming conditions can be used for the reaction shown in FIG. 1G [see, e.g., Satchell and Satchell, *Chem. Soc. Rev.*, 4:231–250 (1975)].

A saccharide monomer of the present invention can be copolymerized with another olefin-type compound in producing a desired copolymer. Such an olefin-type compound is represented by the formula:

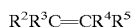

wherein $R^2$, $R^3$, $R^4$ and $R^5$ independently represent H or lower alkyl. Examples of such compounds are as follows.

(i) Hydrophilic olefin-type compounds such as 2-hydroxyethyl methacrylate, 2-hydroxyethyl acrylate, 2-hydroxypropyl methacrylate, 2-hydroxypropyl acrylate, 2-dimethylaminoethyl acrylate or methacrylate, 2-diethylaminoethyl acrylate or methacrylate, 3-dimethylaminopropyl acrylate or methacrylate, 3-diethylaminopropyl acrylate or methacrylate, polyethylene glycol monoacrylate or monomethacrylate, acrylamide, methacrylamide, dimethylacrylamide, dimethylmethacrylamide, acrylic acid and its salts, methacrylic acid and its salts, N-vinylpyrrolidone, vinyl carbazole, and the like;

(ii) Hydrophobic olefin-type compounds including alkyl esters of acrylic or methacrylic acids such as methyl methacrylate, methyl acrylate, ethyl methacrylate, ethyl acrylate, butyl methacrylate, butyl acrylate, amyl methacrylate, amyl acrylate, hexyl methacrylate, hexyl acrylate, octyl methacrylate, octyl acrylate, decyl methacrylate, decyl acrylate, undecyl methacrylate, undecyl acrylate, lauryl methacrylate, lauryl acrylate, stearyl methacrylate, stearyl acrylate, cycloalkyl esters of acrylic or methcrylic acids such as cyclopentyl acrylate or methacrylate, cyclohexyl acrylate or methacrylate, other vinyl compounds such as styrene, vinyl acetate, vinyl propionate, nitriles such as acrylonitrile, etc.;

(iii) Polyfunctional olefin-type compounds such as ethylene glycol diacrylate or dimethacrylate, diethylene glycol diacrylate or dimethacrylate, triethylene glycol diacrylate or dimethacrylate, triethylene glycol diacrylate or dimethacrylate, poly(ethylene glycol)ethylether acrylate or methacrylate (PEGEEM), propylene glycol acrylate or methacrylate, poly(propylene glycol) acrylate or methacrylate (PPGM), vinyl acrylate or methacrylate, allyl acrylate or methacrylate, divinylbenzene, diallylphthalate, trimethylolpropane triacrylate or trimethacrylate, and the like.

A polymerization reaction of the present invention can be conducted by conventional methods such as mass polymerization, solution (or homogeneous) polymerization, suspension polymerization, emulsion polymerization, radiation polymerization (using γ-ray, electron beam or the like), or the like.

For example, a solution polymerization is performed in a solvent in the presence or the absence of a polymerization initiator. Useful initiators are not specifically limited insofar as they are soluble in a solvent. Examples of such initiators are organic solvent-soluble initiators such as benzoyl peroxide, azobisisobutyronitrile (AIBN), di-tertiary butyl peroxide and the like, water soluble initiators such as ammonium persulfate (APS), potassium persulfate and the like, redox-type initiators which are combinations of such initiator and TEMED, $Fe^{2+}$ salt, sodium hydrogensulfite or like reducing agent, etc.

Solvents for use in a polymerization reaction of the present invention are not specifically limited as long as they can dissolve the polymers. Examples of such solvents are water, alcohol, dimethylsulfoxide (DMSO), dimethylformamide (DMF), formamide, and mixtures thereof.

No specific restriction is placed on the mixing ratio of the monomer component, polymerization initiator and solvent to be used in the invention. Preferable to use are less than about 5 parts by weight of the polymerization initiator and an excess amount, preferably about 200 to about 2000 parts by weight, of the solvent, per 100 parts of the monomer component.

The polymerization reaction is preferably conducted in the absence of oxygen. Oxygen can be removed from the reaction system as by usual atmosphere-replacing means such as degassing, nitrogen replacement, and the like. The polymerization reaction is carried out at about 0° to about 90° C., preferably about 20 to 60° C., and is completed in about 20 seconds to 24 hours.

After completion of polymerization, the polymer of the invention can be separated or collected from the reaction product and purified by usual methods. For example, it can be collected by admixing the reaction product with a poor solvent to precipitate the polymer.

A thus obtained polymer of the invention has a molecular weight ranging from hundreds to millions of daltons. The compressibility of a foam prepared according to the principles of the present invention ranges from about 4,000 g/in to about 40,000 g/in.

No specific restriction is placed on a crosslinking agent for use with the present invention, as long as it can crosslink propagating saccharide-(meth)acrylate chains. Examples of useful crosslinking agents are organic polyfunctional isocyanate compounds, polyfunctional epoxy compounds, formalin, glycidol, melamine, silicone oligomer, etc. The amount of the crosslinking agent used is suitably selected over a wide range according to the amount of saccharide monomer desired in the polymer, and the degree of rigidity desired to be imparted to the polymer. For example, in the case of a copolymer of a saccharide-(meth)acryloyl aminocarboxylate and a polyfunctional olefin-type compound, the amount of crosslinking agent used is about 0.5 to 20 parts by weight, per 100 parts by weight of the copolymer.

As discussed hereinbelow, sucrose based hydrophilic and hydrophobic foams which can swell extremely fast have been synthesized and characterized. The most common foaming methods include: thermal decomposition of chemical agent, mechanical whipping, mechanical blowing, volatization of low-boiling liquid, chemical reaction, expansion of dissolved gas upon pressure release, incorporation of microsphere into a polymer mass, and expansion of gas-filled beads by heating. $NaHCO_3$ is preferably used as described herein to generate gas upon reaction with acid.

Existing superabsorbents used in baby diapers are made by a complicated method [U.S. Pat. No. 5,149,335, issued to Kellenberger, et al.] and it involves the use of organic solvents which may raise safety and environment concerns. The method of making sucrofoams described herein can be used to make a wide array of synthetic or natural foams which may be used to replace existing superabsorbents in certain circumstances. Sucrofoams, including other hydrogel foams, are easy to make and show a number of superior properties to the existing products, especially in their swelling rate.

We have also examined various sucrose derivatives to prepare themoreversible hydrogels by copolymerization with hydrophobic comonomers. Sucrose was chosen as a key compoment for this purpose, primarily because it has unique properties in comparision with other natural and synthetic organic reagents. Specifically, sucrose is degradable and absorbable in the body. The hydroxyl groups of sucrose not only serve as good reaction sites for chemical modifications but also make the carbohydrate very water-soluble. The design of sucrose monomers is focused on balancing the hydrophilic and hydrophobic properties so that the synthesized sucrogels exhibited inverse thermosensitivity resulting from the presence of lower critical solution temperature (LCST).

Swelling Ratio

The swelling ratio, Q, is an important parameter for hydrogels and hydrogel foams. It is defined as:

$$Q=(W_s-W_d)/W_d$$

where $W_s$ and $W_d$ are the weights of swollen gel and dried gel, respectively. In addition to the conventional measuring method, we proposed three new methods of measuring Q, each of them having their own advantages and limitations.

Conventionally, $W_s$ is measured by taking the hydrogel out of the swelling medium, gently blotting the hydrogel to remove the excess surface water, and weighing it on a balance. This method is now used by most researchers [Huglin, M, et al. (1984); Davis, T., et al. (1988); Garcia, O., et al. (1994); Jin, X., et al. (1995)]. Its advantage is its flexibility. Q can be easily measured at different temperature and in different swelling media. But it is only good for the firm gels. Highly swollen gels and foams are usually very fragile. Taking them out from the swelling media without breaking them is not always easy. Some researchers measure the size of swollen gel to calculate $W_s$. This approach is difficult for gels with irregular geometry. Even for gels with regular geometric shape, the determination of gel boundary is often difficult.

1. Connector Method

We have developed a simple apparatus similar to that previously described [Dubrovskii, S. A., et al. (1990)]. Briefly, a Buchner funnel was connected to the side arm of a sealed glass bottle by a plastic tubing. The glass bottle served as a reservoir. A finely scaled 10 ml pipet was attached to the top of the glass bottle via a rubber stopper. The height of the glass bottle was adjusted so that the gels in the Buchner funnel were either immersed under water or exposed to the air. During swelling of the gels, the water was absorbed into the gel and the amount of water in the glass bottle was reduced. The reduction in water $(V_0-V_1)$ can be accurately measured from the height of water in the pipette. The volume of water absorbed into the hydrogel $(V_0-V_1)$ was used to calculate $W_s$ and thus Q.

This method is good for all gels and foams since direct handling of specimen is avoided. Furthermore since each measurement is fast and simple, it is especially good for continuous measurement and swelling kinetic studies. However, since the special device needs to be set up, it is not as simple as the other methods. Moreover, the major drawback of this method is that it is not flexible. Changing swelling temperature and swelling media is very inconvenient.

2. Sieve Method

In this method the specimen is placed on a sieve weighing boat which can be easily made by nylon sieve, copper wire, and Teflon tape cover. The sieve weighing boat with the specimen was immersed in swelling media. When Q is measured, the boat was taken out and paper towel was used to remove excess surface water from underneath the sieve. Then the $W_s$ was measured by subtracting the boat weight from the whole weight.

This method is similar to the conventional method. But it avoids handling the specimen. So it is good for both firm gels and fragile gels. Also, it is flexible. It can measure Q at different temperature and swelling media. But it is not very appropriate for foam samples since the suction can take away liquid from the foam matrix.

3. Titration Method

In this method, the specimen is placed in a plastic weighing boat. Swelling solution was added dropwise from a buret. Titration was stopped when free flow liquid appeared. The amount of liquid absorbed was easily read from the buret. This method requires the specimen to absorb the swelling media at a very fast rate. Therefore, it is only good for measuring foam.

Swelling Rate

Figure 2:
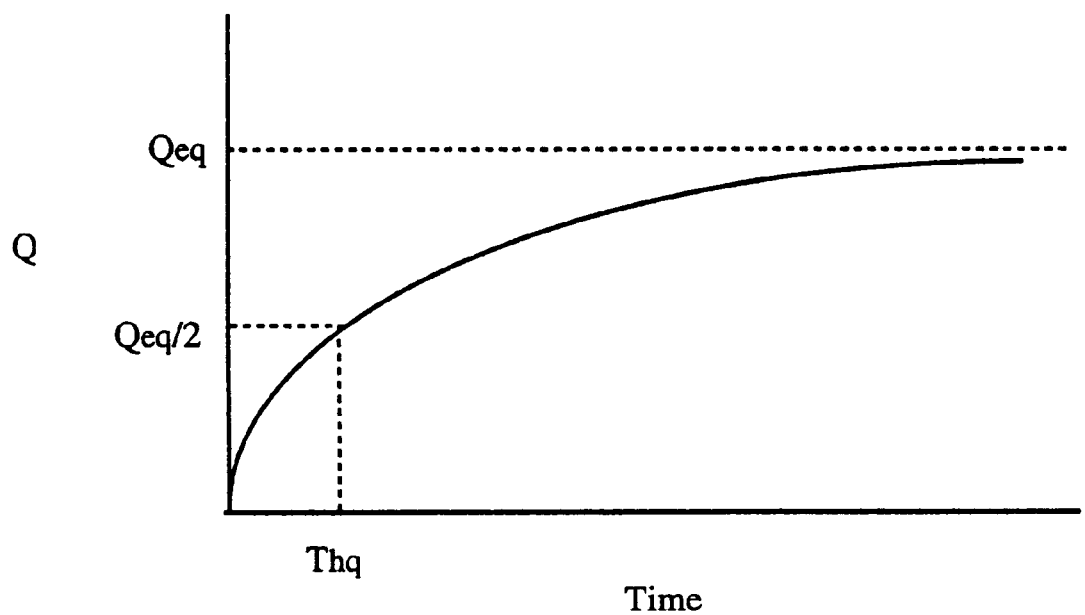
FIG. 2 shows the Thq (time to half equilibrium) measured for the swelling kinetics of hydrogels and foams.

The swelling rate is a critical characteristic of hydrogels and hydrofoams. No standard measuring method, however, has been established. The existing methods are very empirical [see, U.S. Pat. No. 5,149,335]. Some researchers use the time to reach equilibrium swelling as an indicator for swelling rate. The exact point to reach equilibrium swelling, however, is hard to define from the swelling kinetic curve. It is necessary to establish a standard method to compare the swelling rate of different gels and foams. Since the measurement of swelling ratio (Q) is easy and there are several methods available as previously mentioned, we used the time to reach half equilibrium swelling (Thq) as the indicator of swelling rate. From the swelling kinetic curve, this point can be easily and accurately defined (FIG. 2).

Both polymer itself and the structural porosity affect the swelling rate. Wetting agents, however, can somehow change the surface properties of the gels or foams. U.S. Pat. No. 5,149,335 discloses use of Voranol, a polyol, as a wetting agent to increase the gel wettibility and hence increased the swelling rate. In our foam production, Voranol (The Dow Chemical Company) was also added to the sucrofoams to improve the swelling performance.

Part I. Hydrophilic Sucrogels and Sucrofoams
Saccharide Monomer Synthesis

Three different alkylating agents, glycidyl acrylate (GA), glycidyl methacrylate (GM), and 1,2-epoxy-5-hexene (EH) were used to modify sucrose in aqueous solution. Since GM and EH are more hydrophobic than GA, the heterogeneous reaction proceeds very slowly in aqueous solution. Therefore, GA was chosen for the subsequent studies. Tetrabutyl ammonium bromide (TAB), a phase transfer catalyst, was found to greatly accelerate the heterogeneous reaction. But when TAB was used, the pH had to be adjusted to ensure its best performance. The reaction at pH 7.2 was faster than that at pH 6.0 or 9.0. In addition to catalyst and pH, the reaction could also be controlled by changing the reaction ratio, stirring rate, and reaction temperature.

As depicted in FIG. 1 and described in Example I-1, a saccharide (sucrose) reacts with glycidyl acrylate in aqueous solution by opening the epoxy ring to produce a saccharide-GA monomer. The mass spectrum of S-GA monomers so produced, however, showed the presence of a transesterification product. Also, from TLC analysis of the S-GA monomers, the presence of ring-opened GA and acrylic acid was observed. Thus, at least four competing reactions are involved in the S-GA synthesis. The presence of acrylic acid (AA) makes the swelling of gels pH-dependent as described hereinbelow.

The degree of substitution (DS) of glycidyl acrylate (GA) modified saccharides was measured by the bromine method [Edman, P., et al. (1980); Hoppe, H., et al. (1977)] or by the proton-NMR method [Lepisto, M., et al. (1983)]. The proton-NMR method was not very accurate because many peaks were crowded in a small spectral window; however, quantitative C-13 NMR spectroscopy has been suggested as a potential tool for determining the degree of substitution [Akoh, C. C., et al. (1987); Akoh, D. C., et al. (1989)].

The extent of reaction of the S-2.5d monomer was determined from the quantitative C-13 NMR spectrum (see Example I-2) Due to side reactions, the exact degree of substitution could not be obtained from the spectrum. However, by comparing the average peak area of two vinyl carbons (129 and 137 ppm) with the anomeric sucrose carbon at 106 ppm, the extent of reaction could be estimated. Table 1 shows the extent of reaction determined for the four S-GA monomers studied.

TABLE 1

Extent of reaction of S-GA monomers estimated by quantitative C-13 NMR spectra.

| | Extent of reaction |
|---|---|
| S-3h (sucrose: GA = 1:4) | 0.20 |
| S-1.5d (sucrose: GA = 1:1.5) | 0.35 |
| S-2.5d (sucrose: GA = 1:1.5) | 0.47 |
| S-10d (sucrose: GA = 1:8) | 6.7 |

Figure 3:
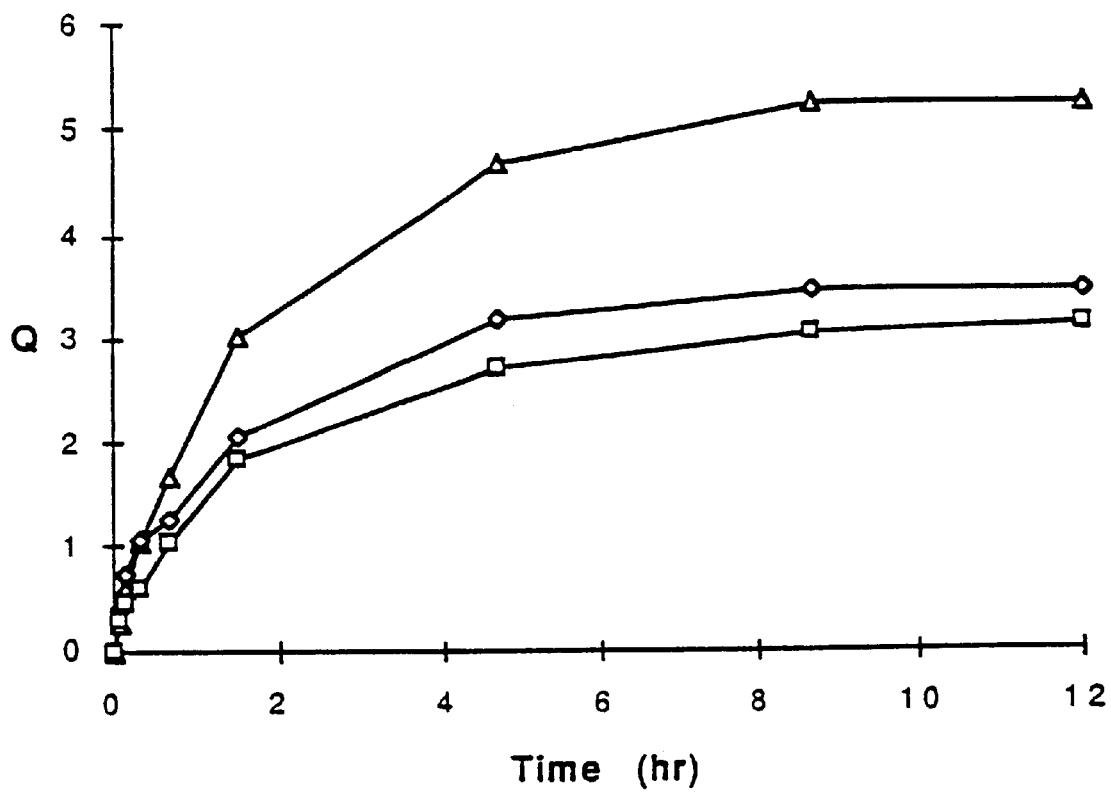
FIG. 3 shows the swelling kinetics of S-2.5d gels in DDW (△), 0.9% NaCl solution (◇), and in 0.03 M HCl solution (□).

The monomers were then polymerized to product hydrophilic sucrogels. (Example I-3)
S-GA Gel Swelling FIG. 3 shows the swelling kinetics of S-2.5d gels in distilled deionized water (DDW), 0.9% NaCl, and 0.03 M HCl solution. These studies were performed as described in Example I-4. The swelling ratios and swelling rates are compared with the S-2.5d foams in Table 2. In saline and HCl solution, the swelling ratios of the gel were lower than those in water. This is believed to be because the side-product AA is also incorporated into the gels—its negative charge at neutral pH caused the gel to swell to a larger extent.

TABLE 2

Comparison of the swelling ratio (Q) and swelling rate (Thq) of sucrogels and sucrofoams with different degree of modification.

| | | S-10d | | S-2.5d | | S-1.5d | | S-3h | |
|---|---|---|---|---|---|---|---|---|---|
| | | gel | foam | gel | foam | gel | foam | gel | foam |
| In DDW | Q | 1.02 | 9 | 5.2 | 52 | 12 | 98 | 27 | 200 |
| | Thq | | 4 sec | 1.2 h | 2 sec | | 2 sec | | 3 sec |
| In 0.9% NaCl solution | Q | | | 3.4 | 33 | | 50 | | |
| | Thq | | | 1.1 h | 2 sec | | 4 sec | | |
| In pH 1.5 HCl solution | Q | | | 2.8 | | | | | |
| | Thq | | | 1.2 h | | | | | |

The swelling properties of foams and gels are compared in Table 2. The foams and gels had big differences in their swelling ratios and swelling rates. Under the same swelling condition, foams usually swelled about 7–10 times larger than the gels. This remarkable difference was due to the unique structural characteristics of the foams. The foams contain numerous empty cells which are dispersed throughout the polymer matrix. When the foams swell in aqueous solution, not only the polymer chains expand with the uptake of water, as in hydrogels, but also numerous empty cells expand to even larger sizes. This accounts for the much higher Q value of foams than hydrogels.

Table 2 also shows that the swelling rates (Thq) of sucrogels and sucrofoams differ greatly. For the gels tested, more than one hour was needed for them to reach the half equilibrium. For the foams, however, only a few seconds were needed. The fast swelling rate of sucrofoams made it difficult to study their swelling kinetics.

There are several factors which contribute to the fast swelling property of foams. First, from the SEM pictures it was observed that the majority of the cells are open cells. These cells are connected to each other throughout the polymer matrix and acted as numerous capillary channels. When the dried foams are placed in aqueous solution, water flows rapidly into the capillary channels and swells the foam. This capillary effect does not exist in ordinary hydrogels.

Kellenberger et al. [U.S. Pat. No. 5,149,335] tried to connect many small hydrogel particles together to form larger particles. By this process, they reportedly introduced some capillary channels into the large particles and greatly increased the swelling rate of the hydrogel particles. However, this method is complicated and only limited capillary channels were introduced. Therefore, the swelling rates of these hydrogel particles were still lower than that of the foams of the present invention. The other important factors which contribute to the fast swelling of hydrofoams are the greater diffusion surface area created by the empty cells and the shorter diffusion distance caused by the very thin cell wall. The swelling process cannot be faster than a diffusion process.

The total amount of solution diffused in the polymer within a unit time (M/t) is proportional to the available diffusion surface area S and inversely proportional to the diffusion distance h:

(M/t S/h)

Since the foams have much larger total surface area S and shorter diffusion distance h, the rate of diffusion of the foams is greatly increased compared with the gels. For the same reason, microsphere hydrogels, having larger surface area and shorter diffusion distance because of their small diameter, can swell to equilibrium within a few minutes compared to the hours required for the larger size hydrogels [Tomlinson, E., et al. (1985)]. However, foam swelling includes another process before the diffusion, which is that water flows through the capillary channels and reaches all the surface area. Alcohol dehydration and the wetting agent enhance the rate of flowing. In fact, some foams swelled so fast that the limiting step in swelling is not the diffusion step but the flowing step.

The crosslinking density can also affect the swelling ratio Q. S-10d foams and gels had higher crosslinking density because they had a higher degree of substitution. The Q value of S-10d foams and gels was much lower than the other three samples. Table 2 shows that the swelling ratio decreases with the increase of substitution. Table 2 also shows that the Q value decreases in saline solution and in acidic solution. This was due to the incorporation of AA in the polymer matrix.

S-GA Foam Synthesis

In the synthesis of foams, surfactants were used not only as a foaming agent but also as a foam stabilizer. A good foam stabilizer should be able to lower the interfacial tension and increase the interfacial film viscosity [Hartley, F. D., et al. (1968)]. These studies are described in more detail in Example I-5. The foaming and foam stabilizing abilities of Pluronic F-127, BSA, and SDS were compared using S-2.5d monomer solution (See Table 3 and Example I-6).

TABLE 3

Comparison of Pluronic F-127, BSA, and SDS as surfactant in S-GA monomer solution. (The solution volume before foam was 0.53 ml)

| Final surfactant concentration (%) | Foam volume (ml) | | |
|---|---|---|---|
| | Peak volume | At 1 min | At 5 min |
| Control | 1.4 | 0.53 | 0.53 |
| Pluronic F-127 | | | |
| 0.05 | 4.6 | 3.8 | 0.62 |
| 0.1 | 4.8 | 4.6 | 0.71 |
| 0.2 | 4.8 | 4.6 | 0.80 |
| 0.35 | 4.5 | 4.3 | 0.98 |
| 0.5 | 4.5 | 4.3 | 1.04 |
| 0.75 | 4.5 | 4.3 | 1.03 |
| BSA | | | |
| 0.01 | 4.3 | 1.0 | 0.53 |
| 0.02 | 4.4 | 2.1 | 0.53 |
| 0.05 | 4.6 | 3.7 | 0.62 |
| 0.1 | 4.6 | 3.8 | 0.63 |
| 0.25 | 4.6 | 3.8 | 0.62 |
| SDS | | | |
| 0.05 | 1.2 | 0.53 | 0.53 |
| 0.1 | 1.1 | 0.53 | 0.53 |
| 0.2 | 1.1 | 0.53 | 0.53 |
| 0.5 | 2.1 | 0.53 | 0.53 |
| 1 | 2.2 | 0.80 | 0.53 |

The peak foam volume represents the foaming ability. Larger peak foam volume suggests a better foaming agent. The foam volumes at 1 minute and 5 minutes reflect the foam stabilizing ability. The longer the foam is sustained, the better foam stabilizer the surfactant is. All three surfactants showed better foaming and foam stabilizing properties compared to the control. SDS, however, was a poor foaming agent and foam stabilizer in the S-GA monomer solution.

Both Pluronic F-127 and BSA were good foaming agents as shown from the peak foam volumes, which were several times larger than the volume of the starting monomer solution. Pluronic F-127, however, was proved to be a better foam stabilizer. At 0.5%, foam did not subside much after 1 minute. Even after 5 minutes, the volume of the foam was still twice that of the starting solution. BSA could only sustain the foam for 1 minute. After that the foam subsided rapidly. From Table 3 it is also seen that at lower concentrations of surfactants, the increase in the surfactant concentration improves the foaming and foam stabilizing effect. But above a certain level, more surfactant does not result in more improvement.

In the S-GA foam synthesis, $NaHCO_3$ was used not only as a blowing agent, i.e., it reacts with acid to release $CO_2$, but also as a pH neutralizer. Polymerization at room temperature using APS and TEMED is pH-dependent. The optimal pH for the initiators is around pH 7–8. The addition of AA reduces the pH to an acidic level which inhibits the initiation of polymerization. Therefore in the absence of $NaHCO_3$, the polymerization proceeds at a very slow rate. This is best shown by the A-B period in the polymerization curve (FIG. 4-A). Upon the addition of $NaHCO_3$, both foam and pH start rising (D-E on the foaming curve), and the polymerization proceeds rapidly (B-C on the polymerization curve).

FIG. 4-A shows two processes, foaming and polymerization, occurring during the foam synthesis. These two processes must be carefully balanced to make foams successfully. First, the polymerization kinetics must be fast. Since the foam stabilizer can only sustain the foam for a few minutes (E-F on the foaming curve), if the polymerization cannot be completed in such a short time, the foam will subside and the gas bubbles will escape (FIG. 4-B). This usually results in smaller foam size or even the formation of gel instead of foam. To achieve fast polymerization kinetics, a good chemical initiator must be used. APS used in our experiment is a very fast initiator when catalyzed by TEMED. Higher reaction temperature and high monomer concentration also help to facilitate the polymerization. Two other circumstances may cause a similar problem. In FIG. 4-A, foaming and polymerization started simultaneously, but in most cases the foaming and polymerization do not begin at the same time. If foaming starts too early, the polymerization may not be fast enough to entrap the gas bubbles. If the foam stabilizer is not very efficient (i.e., the E-F period is too short), the polymerization curve may easily fall behind the foaming curve.

If the foaming curve falls too far behind the polymerization curve, a good foam cannot be synthesized either (FIG. 4-C). This can happen if $NaHCO_3$ is added too late so that polymerization approaches the end. Since very few gas bubbles are generated, the product is essentially a gel with a few closed cells in it. On the other hand, if too much blowing agents (both acid and $NaHCO_3$) are added, there is still a lot of gas generated even when polymerization approaches the end. The excess amount of gas will make the cell wall thin and eventually destroy the foam. The foams formed under this condition usually have large internal void volumes.

In summary, successful synthesis of foams requires careful control of the foaming and polymerization processes in such a way that the polymerization point C falls within foam stabilizing phase E-F (FIG. 4-A). To realize this, the control of timing is critically important. A good surfactant can extend the duration of E-F, and this will make the timing control easier. The formulation in Example 5 was carefully chosen to meet all the requirements to make a good S-GA foam. Several synthetic hydrophilic foams (poly(acrylic acid) foam, polyacrylamide foam, poly(hydroxylpropyl methacrylate) foam) were also successfully synthesized by the same formulation with only slight adjustment. It should be noted that only monomers having fast polymerization kinetics can be used for this method.

Acrylic acid (AA) was used in the foam synthesis. It reacted with $NaHCO_3$ to release fine $CO_2$ gas bubbles and inflate the foam. AA itself, however, can also be incorporated into the polymer matrix. Its negative charge may change the swelling properties of the foam. Table 4 shows the effect of AA on the foam properties. 65 $\mu$l of 6 N HCl and 30 $\mu$l of AA could raise the foam to the same height. The resulting foams showed no difference in their density and swelling rate, Thq. Both swelled extremely fast, but foams formed with AA showed larger Q (swelling ratio) in both water and in 0.9% NaCl solution. This observation is attributed to the electrostatic force caused by the negatively charged AA. Even for the foams blown by HCl, Q in water was larger than that in NaCl solution. This is also attributed to a small amount of AA in the S-2.5d monomer solution.

TABLE 4

Effect of blowing agent on the properties of S-2.5d foams.

| Blowing agent | Density of the dried foam (g/cm$^3$) | Q in 0.9% NaCl solution | Q in DDW | Thq (sec) |
|---|---|---|---|---|
| 30 $\mu$l of AA | 0.11 | 34 | 53 | 2 |
| 65 $\mu$l of 6 N HCl | 0.11 | 22 | 41 | 2 |

In addition to the type of acid, the amount of the acid is also important for the foam properties. These studies are described in Example I-7. Table 5 shows the effect of the amount of AA on the foam properties when the amount of $NaHCO_3$ was maintained constant (42 mg). As the amount of AA increased, the foam became larger so the dried foam size became larger and the density became smaller. As shown in Table 5, Q increased when more blowing agent was used. This was because more empty spaces were generated in foams with more blowing agent. Therefore, these foams could absorb more water and resulted in higher Q. This resulted in a higher swelling ratio.

TABLE 5

Effect of the amount of acrylic acid on the foam properties. (Swelling ratio was measured in 0.9% NaCl solution)

| Acrylic acid (ul) | Peak foam size (ml) | Dry foam density (g/cm$^3$) | Swelling ratio |
|---|---|---|---|
| 5 | 1.0 | 0.60 | 10.4 |
| 10 | 1.6 | 0.30 | 16.9 |
| 15 | 2.5 | 0.12 | 33.7 |
| 30 | 4.2 | 0.09 | 50.6 |
| 50 | 6.5 | 0.07 | 58.0 |
| 80* | 8.1 | 0.53 | 16.0 |

The foams were studied with SEM to determine the effects on their structure of using different amounts of AA. Foams made with 80 $\mu$l AA had an average pore diameter of 530 $\mu$m, which was much larger than that of foams made with 30 $\mu$l AA, i.e., 180 $\mu$m. The same results were observed when HCl was used as blowing agent, i.e., more HCl caused lower foam density and higher Q.

Foams made with 80 $\mu$l of AA did not follow the same trend. In this case, 80 $\mu$l of AA was reacted with 42 mg of $NaHCO_3$ and more gas bubbles were released making the initial foam size larger than all the others. But since AA was in excess after being reacted with $NaHCO_3$, the pH of the solution was very low. This greatly decreased the polymerization rate. Therefore, the foam raised, subsided and eventually collapsed before the polymerization finished. This process is described in FIG. 4-B where gas bubbles cannot be entrapped in the polymer matrix. For this reason, the density of foams with 80 $\mu$l of AA was higher and Q was lower than foams with 50 $\mu$l of AA. Since keeping the solution at higher pH is important to guarantee a fast polymerization rate, an excess amount of $NaHCO_3$ should be used. However, even if a higher pH is maintained, too much gas will weaken the cell wall and even destroy the foam structure as described in FIG. 4-C. Thus, the total amount of blowing agent should be adjusted accordingly.

During the foam synthesis, ingredient A was added to B as described in the Examples. This particular sequence was preferred to make a good foam. When acid solution A was added to $NaHCO_3$ in B, the gas bubbles started from the test tube bottom. Good mixing was achieved and a uniform foam could be easily made. If the sequence was reversed, gas bubbles started from the solution surface, and it would be hard to mix the solution well. Gel instead of uniform foam was usually formed at the bottom of the test tube.

Pressure can affect the foam structure, too, as shown by the studies described in Example I-9. Under pressure, less gas bubbles are released. Therefore, the pore size will be smaller. For instance, the average cell diameter of a S-2.5d foam made in the capped test tube with 80 $\mu$l of AA was about 320 $\mu$m, as compared with the cell diameter of about 530 $\mu$m obtained under atmosphere pressure.

Alcohol dehydration plays an important role in ensuring the fast swell of foams as shown in Example I-10. If a foam is air dried after washing in water, the foam shrinks to a small condensed piece due to the high surface tension of water (72 dyn/cm at room temperature). The polymer chains collapse and close some of the capillary channels. On the other hand, alcohol has a lower surface tension (22 dyn/cm at room temperature) and is a nonsolvent to the S-GA foam. After the dehydration process, water is replaced by alcohol and the polymer chains precipitate in the alcohol and became hardened. The drying process then does not greatly change the foam size. Foams formed in this way had larger pore size and lower density. The average pore size of S-1.5d foam treated with alcohol was much larger than the same foam without alcohol treatment. The number and the size of pores were much greater and this created a great capillary effect. Besides, more and larger pores created much larger total surface area available for diffusion. Also, the cell wall was much thinner and this is expected to provide a shorter diffusion distance. All these accounted for the fast swelling of S-1.5d foams treated with alcohol (Thq=2 seconds when swollen in water) and very slow swelling rate of the foams without alcohol treatment (Thq=~14 minutes when swollen in water). The latter foams still showed faster swelling than the gels (Thq=~1.2 hours when swollen in water) which swelled as a result of diffusion of water through the gel surface.

Wetting agents can change the surface wettability of foams. As disclosed in U.S. Pat. No. 5,149,335, Voranol (a polyol) was used as a wetting agent to increase the swelling rate of polyacrylate hydrogel particles. In the present studies, 1% Voranol 240–800 was found to increase the swelling rate of S-3h foam (Table 6).

TABLE 6

Effect of wetting agent (Voranol 240–800 1% in alcohol) on the swelling rate of foams in 0.9% NaCl solution.

|  | Thq of foams with wetting agent | Thq of foams without wetting agent |
| --- | --- | --- |
| S-3h foam | 3 sec | 6 sec |
| S-2.5d foam | 2 sec | 2 sec |

No improvement was observed for S-2.5d foams. The exact reason for this is not clear yet. In another experiment, Voranol greatly improved the swelling rate of polyacrylamide foams.

Degradation of Gels and Foams

As pointed out previously [Straathof, A. J. J., et al. (1988)], sucrose will not be degraded by invertase as is natural sucrose whenever the fructose ring of the sucrose molecule is modified. In the present studies, sucrogels and sucrofoams were not degraded by invertase, lipase, dipase, acylase, or protease (XXIII) (all from Sigma). In acidic condition, the degradation was slow. No degradation was observed for S-2.5d and S-3h gels even after 2 weeks in 0.1 N HCl at 37° C. (Table 7). A stronger hydrolysis condition, 0.1 N HCl at 90° C., was employed for accelerating the hydrolysis in order to have a rapid understanding of its degradability. These studies are described in Example I-11.

TABLE 7

Degradation time of S-3h gels, S-2.5d gels, and S-2.5d foam under different conditions.

|  | 0.1 N HCl 37° C. | 0.1 N HCl 90° C. | DDW 90° C. | 0.03 N NaOH 37° C. |
| --- | --- | --- | --- | --- |
| S-3h gels | no | 3 days | 9 days | 4 hr |
| S-2.5d gels | no | 9 days | no | 10 days |
| S-2.5d foams | no | 8 days | no | 3 days |

In 0.1 N HCl solution at 90° C., the lower crosslinked S-3h gels degraded within 3 days, whereas the higher crosslinked S-2.5d gels degraded after 9 days. Even the S-2.5d foams degraded very slowly in acidic solution. In DDW, only S-3h gels which had very low crosslinking density degraded after 9 days at 90° C. In basic solution, the degradation process was much faster. In 0.03 N NaOH solution, S-3h gels degraded within 4 hours at 37° C. However, S-2.5d gels, which had higher crosslinking density, still needed 10 days to degrade completely. In contrast, the S-2.5d foams degraded much faster—3 days in the same solution.

Figure 5:
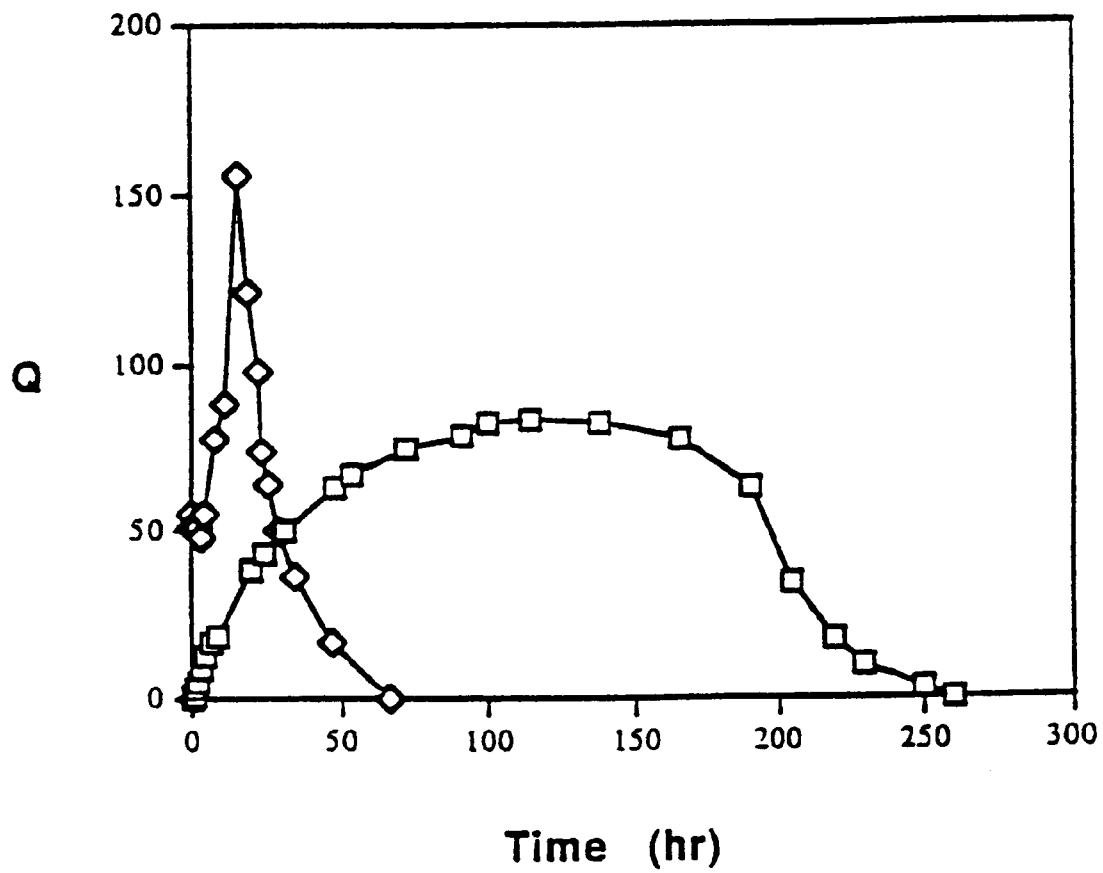
FIG. 5 illustrates the degradation kinetics of S-2.5d gel (□) and foam (◇) in pH 12.5 NaOH solution at 37° C. It took 260 hours to degrade the gel but only 66 hours for the foam.

FIG. 5 depicts the degradation kinetics of the S-2.5d gels and foams. Gels or foams first swelled to absorb the basic solution. Then, as the degradation progressed, some of the crosslinkers were cleaved. This resulted in a lower crosslinking density and higher swelling ratio. Therefore, equilibrium swelling was never reached, i.e., they kept swelling until reaching a point that they were totally dissolved. In the degradation studies, at a certain point, the gels or foams became so flexible that they could pass through the sieve weighing boat used in the degradation studies and dissolved in the basic solution. This is why the measured swelling ratio showed a transient peak in FIG. 5.

The degradation mechanism was studied in Example I-12. The main degradation route for the S-GA gels and foams in base, acid, or DDW is believed to be hydrolysis. Water reacts with ester bonds in the polymer chains, and this leads to the degradation of the polymer. Both base and acid work as catalyst to the hydrolysis. Therefore, the degradation in base or acid is faster than in water. Base hydrolysis and acid hydrolysis have different mechanisms. In basic solution, the degradation occurs very fast at the ester bond. In addition to the hydrolysis of the ester bonds, acid can also cleave the ether linkage between the glucose and fructose ring, but the acid-catalyzed hydrolysis and ether bond cleavage are very slow.

In summary, the degradation rate is dependent on the degradation media, crosslinking density, incubation temperature, and the polymer structure (gel or foam). Basic solution, lower crosslinking density, higher temperature, and foam can promote the degradation.

Compressibility of Foams

Compressibility is an important characteristic for practical application of foams. It represents the pressure endurance of foams after absorbing certain amounts of water. The method used in this study is described in Example I-14, and is a simple way to compare the pressure endurance of different foams. Even though the S-3h foam had a higher swelling ratio (200 in DDW) than S-1.5d foam (98 in DDW), its compression coefficient, K, was lower than that of S-1.5d foam (Table 8). This meant that it had less pressure endurance. This is believed because its crosslinking density is too low to support the foam under pressure. The S-2.5d foam had a lower K value than the S-1.5d foam even though the former had a higher crosslinking density. This is because its swelling ratio was too low (52 in DDW) to hold water tightly. Under pressure, even though the S-2.5d foam did not break, the water was squeezed out. To make foams with a higher pressure endurance, the crosslinking density and the swelling ratio must be properly balanced. Too high or too low a crosslinking density will lead to less pressure endurance.

TABLE 8

Compressibility study of sucrofoams. K, an indicator of the pressure endurance, was calculated by $\Delta W/\Delta D$.

|  | weight range (g) | $\Delta W$ (g) | $\Delta D$ (in) | K (g/in) |
| --- | --- | --- | --- | --- |
| S-3h foams | 110–210 | 100 | 0.014 | 7100 |
| S-1.5d foams | 110–210 | 100 | 0.003 | 33000 |
| S-2.5d foams | 110–210 | 100 | 0.024 | 4200 |

II. Hydrophobic Sucrogels and Sucrofoams

Saccharide Monomer Synthesis

As described in Example II-1, sucrose is reacted with methacrylol chloride and acetyl chloride to make hydrophobic sucrose monomers. An unsuccessful attempt was made to use acrylol chloride instead of methacrylol chloride because acrylate had a faster polymerization rate than methacrylate. But as shown previously [Hickmott, P. W. (1964)], acrylol chloride reacts with alcohols (ROH) in the presence of pyridine in a different way from methacrylol chloride. The main product is a pyridine salt.

The degree of substitution (DS) of sucrose monomers can be easily controlled by changing the reaction ratio of sucrose to methacrylol chloride or acetyl chloride. In the present study, two batches of sucrose monomers, S-H and S-L, were synthesized with higher and lower DS, respectively.

As described in Example II-2, the approximate DS of the S-H monomer was determined from the $^1$H NMR and quantitative C-13 NMR sprectra. From the $CH_3$ group at 18.2 ppm and 20.6 ppm, a DS of 2.25 for methacrylate and 4.74 for acetate was calculated. From the vinyl carbons at 126 and 136 ppm, the DS of methacrylate was found to be 2.46 (average of the two vinyl peaks). From the carbonyl peaks, the DS of methacrylate was calculated as 2.27, whereas the DS of acetate as 4.69 (Table 9).

TABLE 9

Degree of substitution (DS) of methacrylate and acetate groups on S-H and S-L monomers (calculated by quantitative C-13 NMR and proton NMR).

|  |  | quantitative C-13 NMR | | | proton NMR |
|---|---|---|---|---|---|
|  |  | from methyl | from vinyl | from carbonyl | from vinyl |
| S-H monomer | methacrylate | 2.25 | 2.46 | 2.27 | 2.35 |
|  | acetate | 4.74 |  | 4.69 | 4.91 |
| S-L monomer | methacrylate | 0.93 | 0.95 | 0.83 | 0.80 |
|  | acetate | 3.63 |  | 3.64 | 3.85 |

The DS of the S-L monomer was characterized by the same method. The results given in Table 9 show that the DS calculated from different peak integrals were very close. Quantitative C-13 NMR spectra, however, provided clearer peaks (no overlap) and more structural information than the proton NMR spectra.

Characteristic infrared (IR) absorption bands were observed at 3485 $cm^{-1}$ (O—H stretch), 3000–2850 $cm^{-1}$ (C—H stretch), 1751 $cm^{-1}$ and 1726 $cm^{-1}$ (ester C=O stretch). The IR spectral data confirmed the structure of the S-H monomer. The O—H stretch at 3485 $cm^{-1}$ was greatly decreased in contrast to pure sucrose. This was because, on average, more than 7 out of 8 —OH on sucrose were modified by either methacrylate or acetate (from the NMR data). Less than one free hydroxyl group was left on each sucrose molecule. The C=O ester bond absorption at 1751 $cm^{-1}$ was the acetate carbonyl. This peak was larger than the ester bond absorption peak of methacrylate at 1726 $cm^{-1}$. This also conformed to the fact that the DS of acetate was larger than that of methacrylate.

S-H and S-L monomers were easily converted to gels in organic solvents using either chemical or irradiation initiation. These studies are described in Example II-3.

Foam Formation

Both S-H and S-L monomers were not water soluble. In order to make good sucrofoams from these monomers, a good solvent had to be chosen first to dissolve all the ingredients involved in the foam formation. As illustrated above, several requirements must be met to form a good foam. First, fast polymerization kinetics is needed. Thus careful selection of a good initiator system is important. APS and TEMED were used as an initiator system since they showed faster polymerization kinetics than the other initiators (e.g., azo initiators). Higher reaction temperature and higher monomer concentration were also used to increase the polymerization rate. Second, a proper surfactant system with good foaming and foam stabilizing ability must be selected. Third, the acid used to generate gas bubbles is different in different solvent system. Acrylic acid used in S-GA foam could not produce $CO_2$ gas when reacted with $NaHCO_3$ in DMSO solution. Another factor is the control of timing. Higher temperature was used in the synthesis of hydrophobic foams. Under this condition, the initial slow polymerization phase was absent. $NaHCO_3$ was no longer a polymerization trigger as in the synthesis of S-GA foam. The polymerization kinetics of the hydrophobic monomers were also slower than that of the S-GA monomers. All these made the timing control more difficult. The best time to add the $NaHCO_3$ was determined by trial-and-error to ensure that the polymerization was completed in the foam sustaining phase (E-F in FIG. 4-A).

As described in Example II-4, dimethyl sulfoxide (DMSO) was chosen as the solvent for S-H foam formation. It was a good solvent for the S-H monomer and all the other ingredients. Ammonium persulfate (APS) in solid form was found to accelerate polymerization over that in solution. Foam was synthesized at 60° C. to ensure that the polymerization was completed within a few minutes. At room temperature, the polymerization was too slow. The surfactants were chosen from the Silwet surfactant series, Pluronic series, Triton series, Tween and Span series. Two surfactants, Silwet L7605 and Pluronic P105, were found to perform best. Silwet L7605, polyalkylene oxide-modified polydimethylsiloxane, is a silicone surfactant used in the polyurethane industry. Pluronic P105 is a PEO-PPO-PEO triblock copolymer and with the HLB value 12–18. Both surfactants are waxy solids. Either one of them showed good foaming ability but not very good foam stabilizing properties. But when they were properly combined as described in the Examples section, the surfactant system showed a good foam stabilizing property. The possible reason was that one of them worked to decrease the interfacial tension while the other worked to make the foam film tougher. In the DMSO solution, acrylic acid or citric acid could not generate $CO_2$ when mixed with $NaHCO_3$ powder. Thus, a stronger organic acid, p-toluenesulfonic acid solid was used as a blowing agent.

Because the S-H monomers contained many vinyl groups, the crosslinking density of the foam was very high. Therefore, the synthesized foams were brittle as well as fragile, and swelled little in water, methanol, ethanol, acetone, chloroform, and toluene. For this reason, S-L foams which had a lower DS were synthesized. S-L monomer had a lower degree of substitution and was less hydrophobic. Isopropanol was found to be a good solvent to make S-L foam. Silwet L7605 and Pluronic F-127 were chosen from a variety of surfactants and showed best properties. The foams were formed at even higher temperature, 85° C., to ensure fast polymerization. However, the curing was carried out at room temperature. In the synthesis of S-L foams, if curing was carried out at high temperature, more gas would be released and the gas releasing would last even when the polymerization approaches the end. This could destroy the foam structure as shown in FIG. 4-C. In the isopropanol solution, acrylic acid or HCl was used as blowing agent. The swelling ratio Q of S-L foams was 12 in both DDW and 0.9% NaCl solution when HCl was used as a blowing agent. Q was measured by the titration method. This suggested that there was no charge in the polymer matrix. The swelling rate, Thq, in DDW were 10 seconds and 27 seconds with and without the wetting agent treatment, respectively. Thq was measured as described above. Wetting agent increased the swelling rate of the S-L foams, but even with the wetting agent, S-L foams still swelled much slower than those hydrophilic foams (Table 2). The S-L foam was studied by SEM.

As further described in Example II-4, copolymer foams were synthesized by a method similar to the S-L foams. The same surfactants (Silwet 7605 and Pluronic F-127) were used but with a different ratio. HCl was used as a blowing agent. Unlike the open cells observed previously, most of the cells of the copolymer foam were closed. The average pore size was about 150 $\mu$m which was smaller than that of the other foams. This can be explained by fact that less gas was released due to less acid being used.

Degradation of Foams

Figure 6:
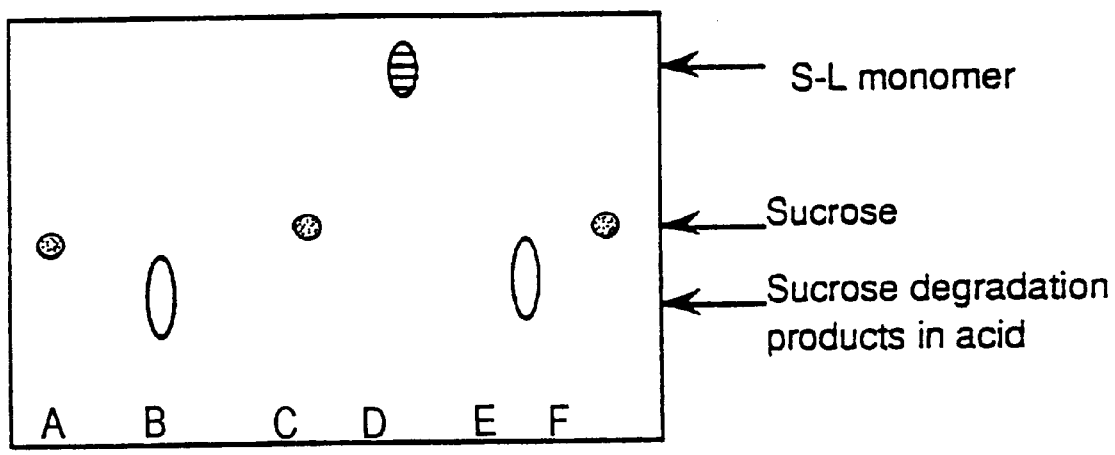
FIG. 6 depicts the degradation mechanism study of S-L using TLC. (A) sucrose; (B) degradation products of sucrose in acid; (C) degradation product of sucrose in base; (D) S-L monomer; (E) degradation products of S-L foam in acid; (F) degradation product of S-L foam in base.

S-L foam showed little degradation in 1 N HCl solution at 90° C. even after one month, but in 1 N NaOH solution at 90° C., it was degraded within 12 hours. These studies are described in Example II-5. FIG. 6 illustrates a TLC plate showing the degradation mechanism in acidic and basic solution. Spot A was pure sucrose. Spot B was the degradation products (glucose and fructose) of sucrose in acid. Spot C was the spot of sucrose after being incubated in basic solution. It showed that sucrose was not degraded by basic solution. Spot D was the hydrophobic S-L monomer. Spot E was the degradation product of S-L foam in 1N HCl. Even though the degradation was not significant, it still showed some spots the same as the degradation products of sucrose in acidic solution. This suggested the degradation mechanism involved both the ester bond cleavage and the ether bond (between the glucose and fructose ring) cleavage in acid. If only the second mechanism existed, the degradation products should have contained glucose acetate and fructose acetate which had higher rf value than the sucrose. These spots were not observed on the TLC plate. From the TLC study, however, we could not confirm whether these two mechanisms worked simultaneously or the ether bond cleavage happened only after the ester bonds were cleaved. Spot F was the degradation product of S-L foam in a basic solution. Sucrose was the final degradation product. This meant the ester bond hydrolysis was the only mechanism in basic solution. Since the base catalyzed hydrolysis had much higher kinetics, the degradation of S-L foam in base was much faster.

III. Thermoreversible Saccharide Monomers

Synthesis of S-N-methacryloyl aminocarboxylate monomers

Two separate reactions were used in the synthesis of thermoreversible saccharide monomers, as exemplified with sucrose. First, substituents that esterify sucrose are obtained. The method of controlling the hydrophobicity of substituent molecules was considered, since hydrophobic properties are necessary to make thermoreversible hydrogels.

Sucrose substituents can be synthesized fast and with ease by the Schotten-Bauman reaction. As shown in Example III-1, under basic conditions, methacryloyl chloride reacts with amine groups of 6-aminocaproic acid, leucine, and 11-aminoundecanoic acid to form amide bonds. The choice of N-amino carboxylic acids with various carbon lengths made it possible to control the hydrophobicity of sucrose monomers to a certain extent. One practical advantage of this approach is that various amino acids can be utilized for the preparation of sucrose monomers having different properties.

In the second step, the substituents are reacted with sucrose by the Mitsunobu reaction. Advantages of the Mitsunobu reaction in the esterification of sucrose have been discussed previously [Abouhilale, S., et al. (1991)]. The Mitsunobu reaction does not require that the medium be basic which generally results in undesirable side-reactions such as acyl migration. The Mitsunobu reaction proceeds fast even at room temperature and esterifies only primary hydroxyl groups. Since sucrose has three primary hydroxyl groups, the resultant sucrose derivatives can be used as a crosslinking agent in the synthesis of sucrose hydrogels. This step is described in more detail in Example III-2.

Synthesized sucrose monomers (MACS, DMACS, MLS, and MAUS) were characterized by NMR. Structural formulas for these compounds are shown in FIG. 7. The $^{13}$C-NMR data showed that the most favorable site for esterification in sucrose was OH-6, since the first substituent always reacted with it first. This observation is consistent with the previous study [Abouhilale et al. (1991)] who synthesized polyfluorinated 6-esters of sucrose with the Mitsunobu reaction. All of the carbon peaks and some proton peaks from sucrose were identified on the basis of their results. In the synthesis of DMACS, the molar ratio of sucrose:N-methacryl-6-aminocaproic acid was 1:1.5. The $^{13}$C-NMR spectrum of purified DMAC showed that two N-methacryloyl-6-aminocaproyl groups were attached to C-6 and C-6'. The C-5' peak (83.9 ppm) and the C-6' peak (64.1 ppm) of sucrose shifted to upfield by 3 ppm and 2.7 ppm, respectively. These shifts are consistent with those reported elsewhere [Jansson et al., (1987)] in the modification of glucose. The previous results showed that the introduction of an O-acetyl group in any position of a glycopyranoside caused deshielding of the substituted carbon by 0.7–3.5 ppm and shielding of the carbons next to this carbons (b carbons) by 1.2–2.8 ppm. Other evidence for the disubstitution of DMACS was that two ester carbons were identified by two peaks at 175.1 and 175.3 ppm.

The degree of substitution of DMACS was also calculated from integration of $^1$H-NMR peaks. When a special decoupling agent is used, $^{13}$C-NMR also provides quantitative information on the number of carbons. The integrated $^{13}$C-NMR spectrum of DMACS showed that the integration value of substituent carbon peaks was about twice that of sucrose peaks. The data of elemental analysis were also close to theoretically calculated values.

Temperature-Dependent Swelling Profiles

As described in Example III-3, sucrose monomers were copolymerized with commercially available hydrophobic monomers such as PPGM and PEGEEM to make thermoreversible hydrogels. The formation of hydrogels was tested by polymerization of monomer mixtures with different amounts of DMACS, a crosslinking agent. The monomer mixture of MACS and PPGM formed a gel at low concentration and even in the absence of DMACS. As the polymerization proceeded, polymer chains containing PPGM and MACS might entangle each other significantly to form a gel even in the absence of DMACS. MLS which has a leucyl group, however, needed a relatively large amount of DMACS. At 5 mole % of DMACS, a very fragile hydrogel of poly(MLS-co-PPGM) formed. In subsequent studies, MACS-containing sucrogels were crosslinked with 0.5 mole % of DMACS, while MLS-containing sucrogels were crosslinked with 10 mole % of DMACS.

The composition of hydrogels was varied by adjusting the amount of sucrose monomers. The amount of sucrose monomers in hydrogels influences the hydrophilicity (or hydrophobicity) of hydrogels. The molar ratios of sucrose monomer:PPGM were 2:1, 2:2, 2:3, and 2:4. As described in Example III-4, the temperature dependence of these sucrogels was investigated by examining the temperature-dependent swelling and swelling kinetics.

Figure 8:
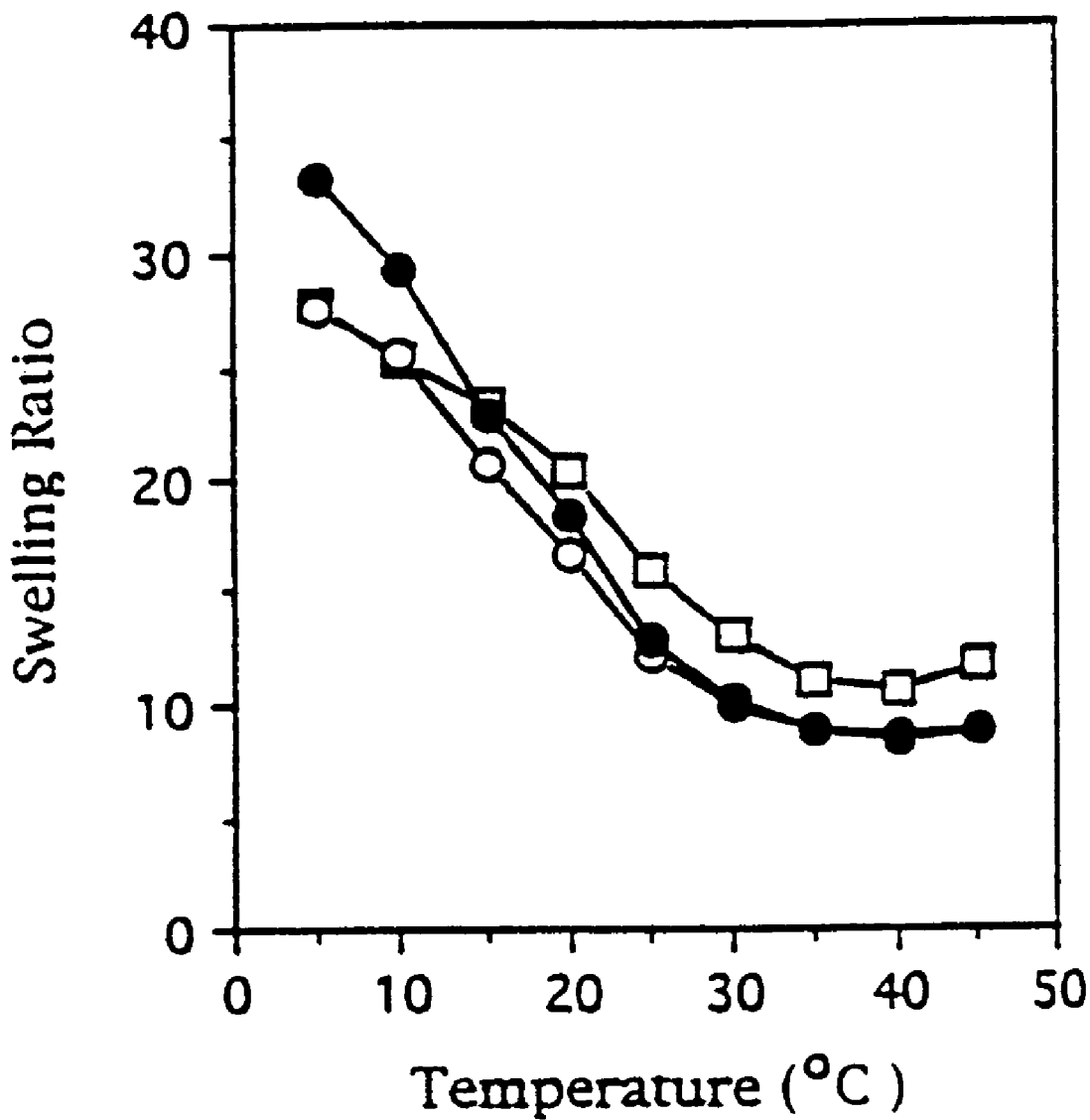
FIG. 8 depicts the thermosensitive volume change of sucrogels made of MACS and PPGM. The gels were cross linked with DMACS. The molar ratios of MACS:PPGM were 2:4 (●), 2:3 (○), and 2:2 (□).
Figure 9:
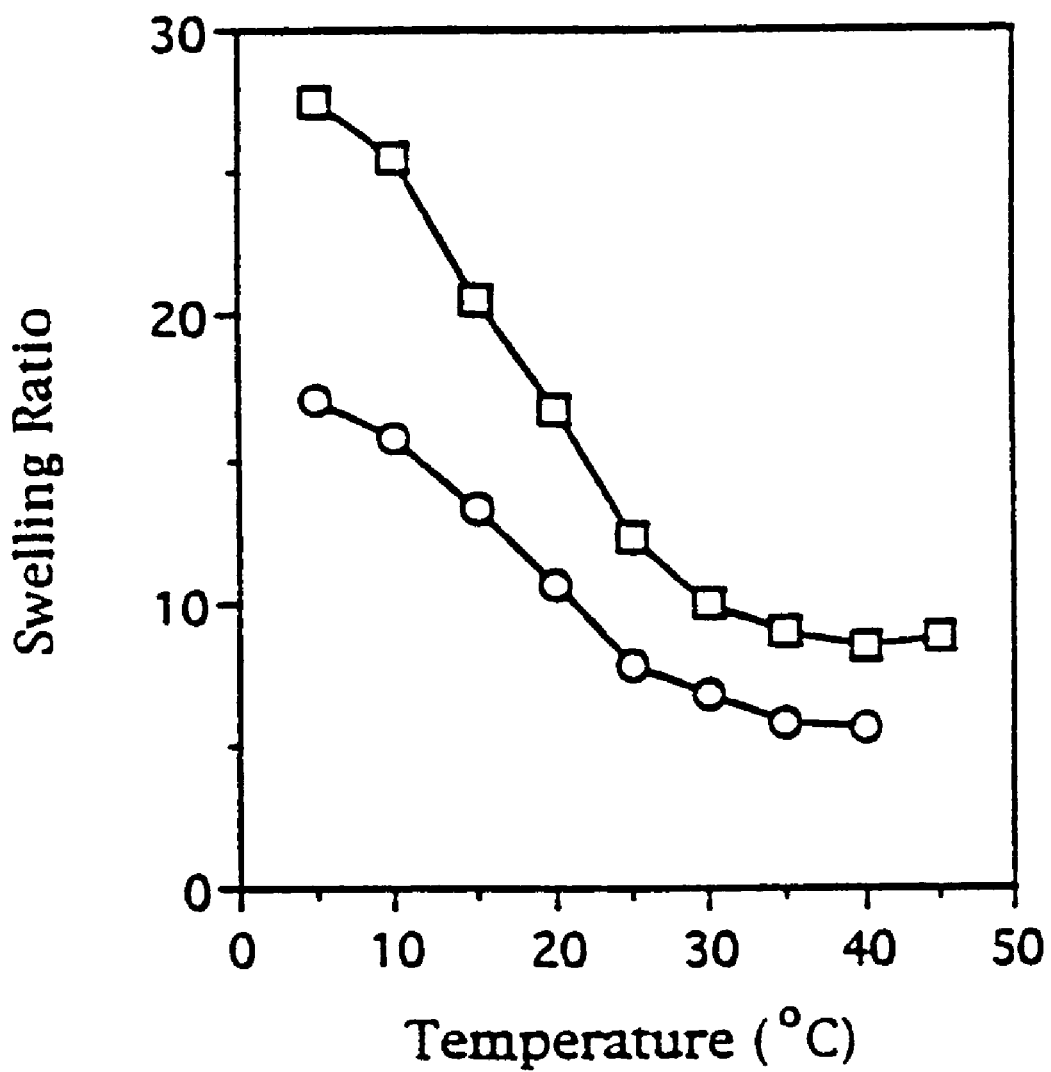
FIG. 9 depicts the effect of crosslinking agent (DMACS) on the thermosensitive volume change of hydrogels made of MACS and PPGM. The molar ratios of MACS:PPGM was 2:3. The concentrations of DMACS were 0.5 mole % (□) and 5.0 mole % (○).

Sucrogels made of MACS and PPGM or DMACS and PPGM shrank as the temperature increased. As shown in FIG. 8, the volume decrease with an increase in temperature was gradual. Volume continued to decrease monotonically until the temperature reached 35° C. The maximum of swelling ratio at 5° C. was around 30, and the exact value was dependent on the concentration of sucrose monomers. As the concentration of sucrose monomers increased, the maximum of swelling ratio at 5° C. decreased and the minimum swelling ratio at 35° C. increased slightly without a clear change in the overall profile. This may be due in part to the increase in hydrophilicity of hydrogel by increased sucrose monomers. When the concentration of DMACS was increased from 0.5 mole % to 5.0 mole %, swelling of the sucrogels decreased while the overall thermosensitive swelling profiles remained very similar (FIG. 9). Higher crosslinking density restricts the swelling of hydrogels by forming tighter networks of polymer chains.

Figure 10:
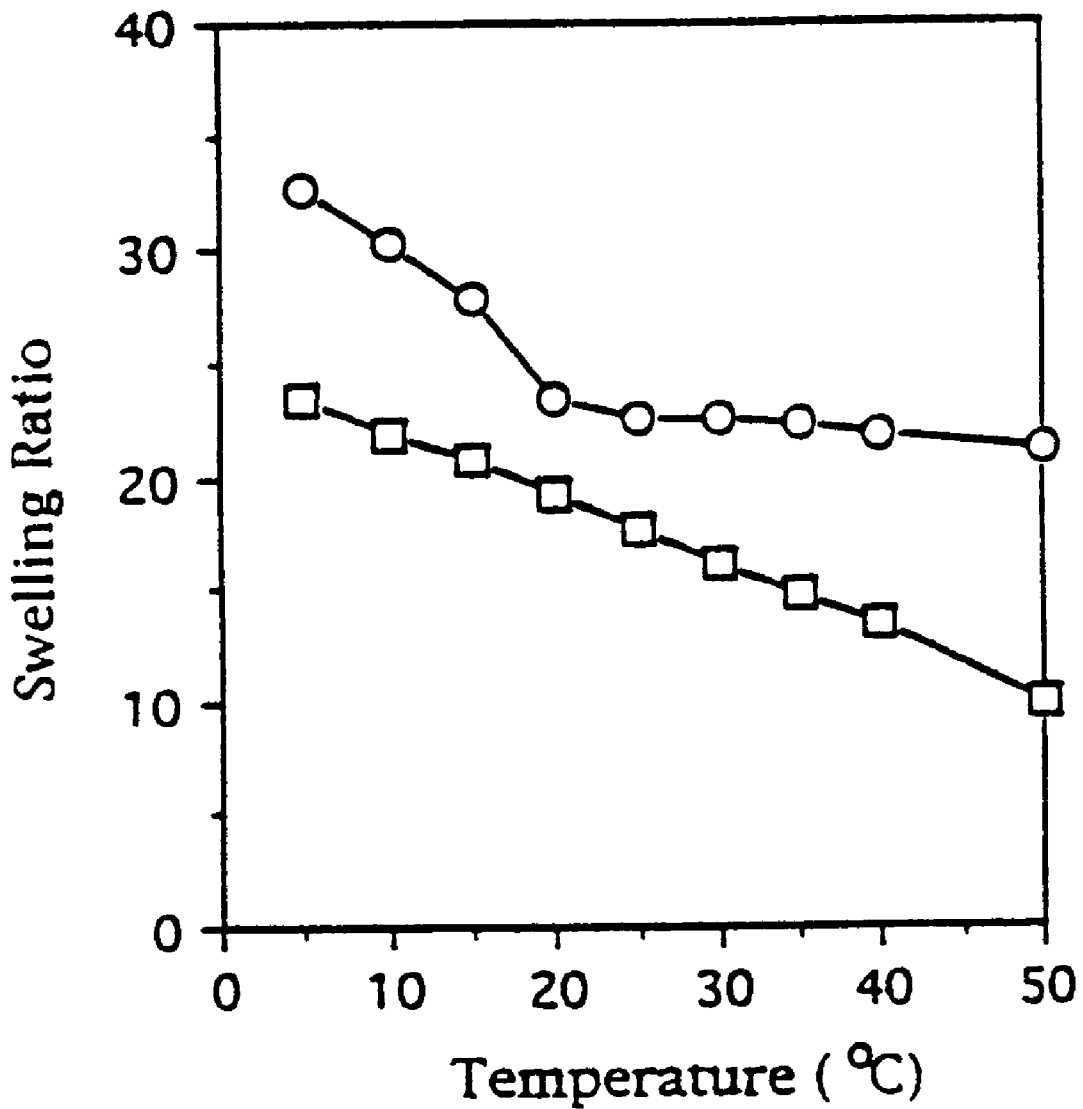
FIG. 10 depicts the thermosensitive changes in volume of hydrogels made of PEGEEM only (○) and MACS-PEGEEM copolymers (□). The molar ratio of MACS-PEGEEM was 1:1 and the sucrogels were formed using DMACS as a crosslinking agent.

Thermoresponsive hydrogels were also prepared by copolymerization of MACS and PEGEEM in the presence of DMACS. This type of thermosensitive sucrogels showed a linear decrease in swelling ratio as temperature increased (FIG. 10). The thermosensitive property of MACS-PEGEEM sucrogels was quite unique in that a linear decrease in volume change was observed in the temperature range of 5° C. to 50° C. On the other hand, hydrogels composed of only PEGEEM showed a little thermosensitive property until the temperature increased to 20° C. and volume did not change as the temperature increased above 20° C. The observed property in which the swelling ratio of the MACS-PEGEEM sucrogels is a linear function of the temperature is expected to have wide applications.

Figure 11:
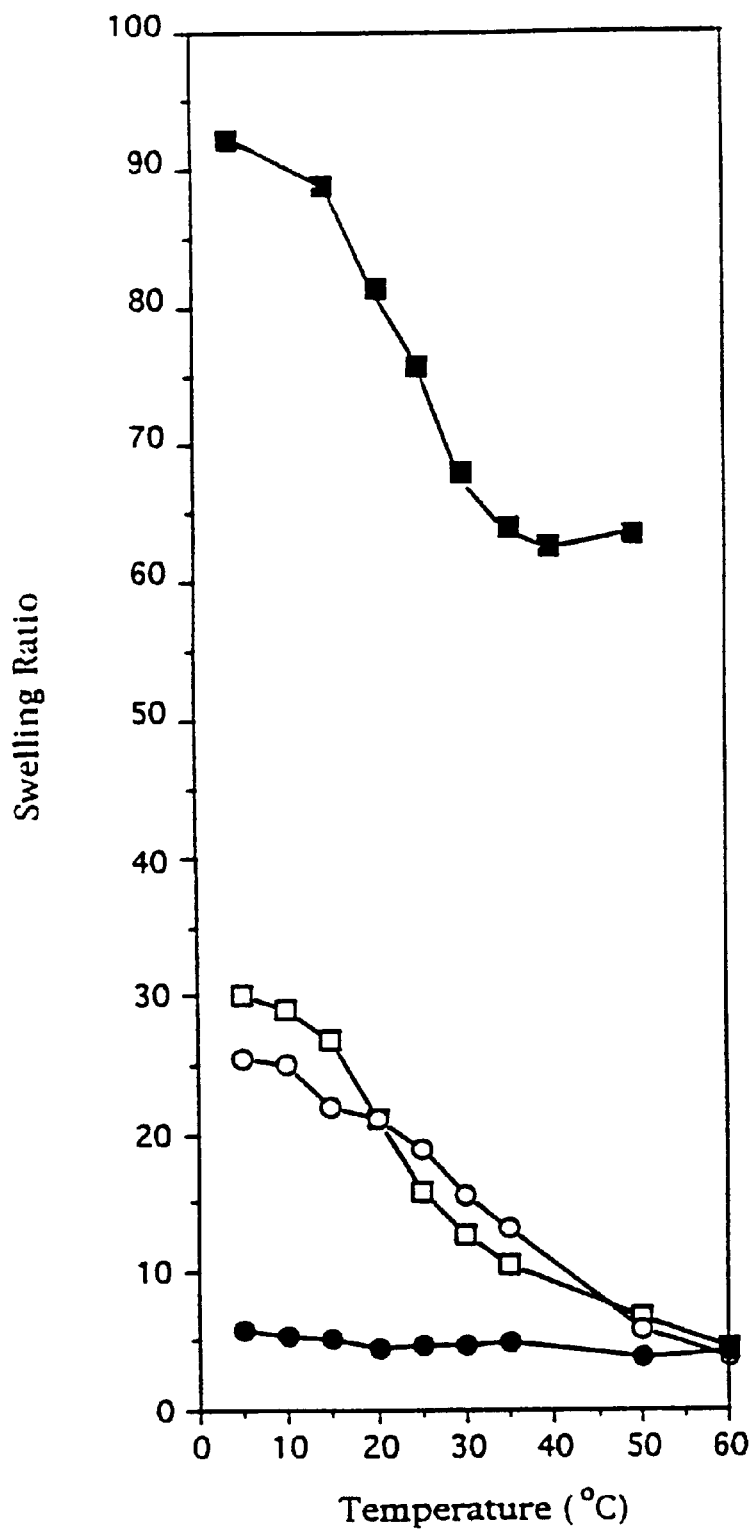
FIG. 11 depicts the thermosensitive changes in volume of hydrogels made of PPGM only (●), MLS-PPGM (□), and MLS-PEGEEM (○) copolymers. The molar ratios of MLS-PPGM were 1:1 and 2:1 (■) and that of MLS-PEGEEM was 1:1. The sucrogels were formed using DMACS as a crosslinking agent.

Another type of thermosensitive sucrogel was synthesized by copolymerization MLS and PPGM (or PEGEEM) using 10 mole % of DMACS as a crosslinking agent. The molar ratio of MLS:PPGM was either 1:1 or 2:1. Hydrogels made of only PPGM were not temperature sensitive at all and the swelling ratio was quite low (around 5) in the temperature ranging from 5° C. to 60° C. (FIG. 11). The MLS-PPGM and MLS-PEGEEM sucrogels, however, showed inverse thermosensitive properties in the same temperature range. The MLS-PPGM sucrogels had a rather clear volume transition between 20° C. and 30° C., while the MLS-PEGEEM sucrogels showed almost a linear volume transition between 10° C. and 60° C. When the concentration of sucrose monomers in the sucrogels increased, the maximum swelling ratio of the gels increased dramatically from 30 to 90. As shown in FIG. 11, the overall thermosensitive profile remained unchanged.

Thermoreversible Properties of Sucrogels

The thermoreversibility of swelling and shrinking of sucrogels were investigated by measuring the swelling ratio as a function of time at two different temperatures. When sucrogels previously equilibrated at 4° C. were placed into the container maintained at 60° C., sucrogels underwent a volume decrease immediately (FIG. 12). Shrinking of sucrogels at 60° C. was much faster than swelling at 5° C. Sucrogels made of different sucrose monomers and different hydrophobic monomers showed the same behavior except that the swelling ratios were different. In general, shrinking to an equilibrium at 60° C. requires only 2–6 h, while equilibrium swelling at 5° C. took 2–3 days. The slow swelling compared to shrinking of hydrogels is observed for almost all hydrogels. This is probably due to the fact that swelling requires relaxation of entangled polymer chains.

As shown in FIG. 12, the swelling and shrinking profiles were reproduced in subsequent swelling-shrinking cycle. The use of different types of sucrose monomer (MACS, MLS, or MAUS) and hydrophobic monomers did not alter the overall profile, but only the swelling ratio was changed. The change in crosslinking agent also changed only the swelling ratio, while the overall thermosensitive property remain the same. Of the three sucrose monomers examined, the MAUS-PEGEEM sucrogels showed the lowest swelling ratio under the same condition.

Studies on the swelling kinetics and the thermoreversible properties showed that the most important parameter controlling the thermosensitivity was the type of sucrose monomer. It appears that the thermosensitive properties of sucrogels result from a combination of hydrophobic side chains and the hydrophilic and bulky sucrose moiety of the sucrose monomers. The thermosensitivity of these sucrogels can be controlled by adjusting various factors such as length and the bulkiness of side chains of the polymer backbone. Thus, various amino acids can be used in the preparation of sucrose monomers and these will provide sucrogels with different thermosensitive properties. It is interesting to note that some sucrogels showed linear thermosensitive properties while others showed s-shaped thermosensitivity. These properties can be applied in various fields including controlled drug delivery and biotechnology.

Degradation of Thermoreversible Hydrogels

The degradation of MACS-PPGM sucrogels in acidic (pH 2) and basic (pH 12) solutions was examined in Example III-5. Sucrogels degraded much faster in basic condition than in acid. The sucrogels degraded completely within 2 h in pH 12 solution (FIG. 13A), while it took about 20 days for 80% degradation in pH 2 solution (FIG. 13B). The difference in degradation rates is most likely due to the intrinsic lability of ester linkages in the presence of base and subsequent formation of anions. The electrostatic repulsion by the formed anions likely caused swelling of the partially degraded hydrogel, which in turn made the base-catalyzed hydrolysis easier.

Degradation sites by acid and base were examined by TLC. In the case of degradation in basic solution, intact sucrose was detected by TLC after the complete degradation of hydrogel. On the other hand, the degradation sucrogels by acid did not show the intact sucrose band on TLC. The cleavage site of sucrogels by base may be ester linkages which are part of sucrose monomers or hydrophobic monomers. On the other hand, cleavage at the ether linkage of sucrose is most likely in acid.

SEM Observation of Thermoreversible Hydrogels

The structure of sucrogels was visualized by SEM after freeze drying of sucrogels, although the preparation of SEM samples was rather problematic. Because of the temperature-dependent volume changes of the prepared sucrogels, heat could not be used to prepare dried sucrogel specimens for SEM observations. Thus, as described in Example III-6, water was removed by freeze drying.

The pore size of MLS-PPGM sucrogels (MLS:PPGM= 1:1) decreased as the sucrogels were exposed to 60° C. water for a longer period of time. After the treatment of sucrogels with 60° C. water for 20 sec, the size of pores at the surface and inside of the hydrogel matrix was rather homogeneous. As the sucrogels were treated with 60° C. water for 1 day, the pore size decreased drastically. The pore size distribution was still homogeneous.

The effect of temperature on the pore size of the MACS-PPGM sucrogels (MACS:PPGM=1:1) was similar to that of the MLS-PPGM sucrogels. The inside of the MACS-PPGM sucrogels was not observed well because of the collapse of the gel matrix during the freeze drying procedure. The collapse could have been due to the low concentration of the crosslinking agent. There was no visible difference in pore sizes between the surface and the inside of sucrogels.

CONCLUSION

Hydrophilic saccharide monomers can be synthesized by reaction with glycidyl acrylate, glycidyl methacrylate, or 1,2-epoxy-5-hexene in aqueous solution. Phase transfer catalysts can accelerate these reactions. The degree of substitution can be controlled by changing the reaction ratio, reaction time, reaction temperature, and stirring rate. Hydrogels with different crosslinking density have different swelling properties.

S-GA sucrofoams have a much larger swelling ratio and faster swelling rate than sucrogels. Alcohol dehydration and wetting agent can promote fast swelling. Several factors (polymerization rate, amount of gas released, timing, and surfactant) must be carefully controlled to ensure good foam formation. The type and amount of acid can change the swelling property of sucrofoams. The pressure endurance of sucrofoams is related to the crosslinking density and the equilibrium swelling ratio. The degradation of S-GA gels and foam was much faster in basic solution than in acidic solution.

Hydrophobic sucrose monomers with different degrees of substitution can be synthesized by varying the reaction ratio of sucrose to methacrylol chloride and acetyl chloride. The degree of substitution can be determined from proton and quantitative $^{13}C$ NMR spectra. Synthesis of hydrophobic sucrofoams needs even more careful control. The degradation of hydrophobic sucrofoams is also faster in basic solution than in acidic solution. The degradation mechanism in basic solution is hydrolysis of the ester bond. In acidic solution, cleavage of both ester and ether bond hydrolysis is involved.

Sucrose monomers also were copolymerized with hydrophobic monomers to produce inverse thermoreversible sucrogels. Thermoreversible sucrogels exhibited reversible volume changes as the temperature was altered, and the thermoreversible process was reproducible. The thermosensitive sucrogels were degraded in both acidic and basic conditions. These biodegradable, thermoreversible sucrogels are expected to find various applications in diverse fields including controlled drug delivery and biotechnology.

The present invention will now be described with reference to certain examples, which illustrate, but do not limit, the invention.

EXAMPLES

Unless otherwise mentioned, chemical reagents were obtained from Aldrich Chemical Co. (Milwaukee, Wis.). Sucrose was obtained from Aldrich or J. T. Baker (Phillipsburg, N.J.). Methacryloyl chloride was purified with distillation at 150° C. before use. Other organic solvents and chemicals used were reagent grade. Silica gel thin layer chromatography (TLC) plates (UNIPLATE) were obtained from Analtech, Inc. (Newark, Del.). Charring agent for TLC (Sigma spray agent, sulfuric acid) was obtained from Sigma Chemical Co. (St. Louis, Mo.).

I. Hydrophilic Sucrogels and Sucrofoams

Example I-1
Synthesis of Sucrose Acrylate (S-GA) Monomers

Four batches of sucrose acrylate monomers were prepared. For each batch, 10 g of sucrose, 1.9 g of TAB (99%), and a small amount of p-methoxyphenol, which was used as a polymerization inhibitor, were dissolved in 20 ml phosphate buffered aqueous solution (pH 7.2, 0.05 M) in a 200 ml Erlenmeyer flask equipped with magnetic stirrer. The TAB was used as a phase transfer catalyst. Glycidyl acrylate (GA) (Lancaster Synthesis, Inc.; Windham, N.H.) was added to each batch to make sucrose:GA ratios of 1:4, 1:1.5, 1:1.5, and 1:8. The reaction was performed at room temperature with continuous stirring and the flasks were covered with aluminum foil to avoid the light.

The four batches were allowed to react for 3 hours (sucrose:GA=1:4), 1.5 days (sucrose:GA=1:1.5), 2.5 days (sucrose:GA=1:1.5), and 10 days (sucrose:GA=1:8), and were assigned the designations S-3h, S-1.5d, S-2.5d, and S-10d, respectively. Each reaction was stopped by addition of 70 ml methylene chloride followed by extraction. The water phase was further extracted with methylene chloride four times to remove unreacted GA. The reaction mixtures were tested on TLC to ensure that no unreacted GA remained.

Since the reaction is not stereospecific, the reaction mixture contained unreacted sucrose, mono-, di-, and multi-substituted sucrose. In addition, there were some impurities such as acrylic acid (AA) resulting from side reactions. Since preparative separation was difficult, the mixtures were used to make gels and foams without further purification.

Example I-2
Extent of Reaction by Quantitative $^{13}C$ NMR

The extent of reaction for each of the sucrose acrylate monomer batches prepared in Example 1 was examined by the quantitative $^{13}C$ NMR technique. 1 ml sucrose monomer was dried in vacuum. To this were added $D_2O$, 15 mg of chromium (III) disodium pentetate (final concentration of 0.025 M), a spin-lattice relaxation reagent, and 10 mg of 3-(trimethyl silyl)-1-propanesulfonic acid (sodium salt), a water soluble internal standard. Gate-decoupled pulse sequence was used to eliminate the NOE effect. The average area of double bond peaks at 128 and 134 ppm was compared with the area of the anomeric sucrose carbon peak at 106 ppm. The ratio reflected the reaction extent.

Since S-10d was only slightly soluble in $D_2O$, methanol-D was used as solvent. The other three monomers were dissolved in $D_2O$.

Example I-3
Gel Formation

S-GA gels were prepared either by γ-irradiation or by chemical initiation. When γ-irradiation was used, the total dose ranging from 0.008 Mrad to 0.24 Mrad were applied to the S-GA monomers in clean glass test tubes. When chemical initiation was used, 30 μl of 10% ammonium persulfate (APS) in distilled deionized water (DDW) and 30 μl of 10% N,N,N',N'-tetramethylethylenediamine (TEMED) (BioRad, Richmond, Calif.) in DDW were added to 1 ml of S-GA monomers. Sucrogels formed within 20 seconds to 2 minutes. The gels were washed with a copious amount of DDW for 10 days to remove nonpolymerized impurities and unreacted sucrose and then were dried in a 60° C. oven or food dehydrator to a constant weight. S-GA monomer concentration (excluding all the nonpolymerizable impurities) was determined by dividing the dried gel weight by the weight of monomer solution used. The concentration of S-2.5d monomer solution was determined to be 18%.

Example I-4
Swelling Kinetics of the Sucrogels

To characterize the swelling behavior of the S-GA gels produced in Example 3, 200 mg of dried gels were allowed to swell in DDW, 0.9% NaCl solution, and 0.03 M HCl solution, respectively. At given time intervals, Q (swelling ratio) was measured by the conventional method.

Example I-5
S-GA Foam Synthesis

All four batches of S-GA monomers were used to synthesize sucrofoams. The following formulation was applied to all the synthesized sucrofoams.

A: 1 ml monomer solution+67 μl of 5% Pluronic F-127 in DDW+100 μl of 10% ammonium persulfate (APS) in DDW+30 μl of acrylic acid (AA)+67 μl of 10% TEMED in DDW.

B: 85 mg of $NaHCO_3$ powder+33 μl of 5% Pluronic F-127 in DDW+33 μl of 10% TEMED in DDW.

Ingredient A is added to ingredient B in a 14 ml plastic test tube (Falcon, 17×100 mm), with vigorous stirring for 2–5 seconds. The solution started foaming and rising, and after 15–60 seconds, bubbling stopped and the foam settled. The foam was allowed to cure at room temperature 10 more minutes. The foam was then retrieved and washed with copious amount of water. The swollen foam was then dehydrated in absolute alcohol containing 1% Voranol 240–800 (as a wetting agent). After repeated dehydration for several times, water was replaced by alcohol. The foam was then dried in a 60° C. oven or in a food dehydrator to a constant weight. In this formulation, AA was used as a blowing agent. 65 μl of 6 N HCl, which can raise the foam to the same extent, can be used to replace 30 μl of AA. In the following studies, unless specifically mentioned, all the foams were made with the above formulation using AA as a blowing agent.

Example I-6
Comparison of Surfactants in the Synthesis of S-2.5d Foam

Pluronic F-127 (BASF; Parsippany, N.J.), bovine serum albumin (BSA), and sodium dodecyl sulfate (SDS) (BioRad) were compared in terms of their ability to form and stabilize the foam. Pluronic surfactants are PEO-PPO-PEO triblock copolymers, and are nontoxic and nonionic surfactants. Pluronic F-127, having a hydrophilic lipophilic balance (HLB) value 18–23, was chosen from 35 Pluronic surfactants, since it showed the best properties. BSA was selected as a biodegradable protein surfactant. SDS has long been used as an excellent surfactant in aqueous systems.

To 0.5 ml of S-2.5d monomer solution in a 12×75 mm graduated plastic test tube was added 15 μl of AA and surfactant solution to make the final volume of 0.53 ml. 42 mg of $NaHCO_3$ powder was added to each test tube and stirred vigorously for 2–5 seconds. Foam was formed and rose immediately and reached the maximum volume within several seconds and then started to subside. The volumes at maximum point, at 1 minute and at 5 minutes were recorded, respectively.

Example I-7
Effect of Amount of Acid on the Sucrofoams

Six batches of S-2.5d foams were prepared according to the method described above except that the amount of AA was varied and the amount of all the other ingredients was halved. The density of the dried foam was calculated by the formula:

$$D=W_d/V_d$$

where $W_d$ is the weight of dried foam and $V_d$ is the volume of the dried foam. $V_d$ was determined by immersing the dried foam into mineral oil (or any other solvent in which the foam would not swell) in a graduated cylinder and then removing it from the mineral oil. The volume change was taken to be the volume of the dried foam. The swelling ratios of the foams were determined by the titration method.

Example I-8
Effect of Type of Acid (AA or HCl) on the Swelling Properties of S-2.5d Foams When AA was used as a blowing agent, it was incorporated in the polymer matrix. The ionizable AA can somehow alter the swelling properties of the foam. When 65 μl of 6 N HCl was used, the same foam size was obtained. The foams made with these two blowing agents were compared in terms of their density, Q, and Thq.

According to the definition of Thq, the weight of swelling media needed for the Thq test is expressed as $W_d \times Q/2$, where $W_d$ is the weight of the dried gel or foam. The swelling solution was added to a polystyrene weighing boat containing the foam. The time needed for the foam to absorb all the solution was recorded as Thq.

Example I-9
Effect of Pressure on the Foam Structure

In the process of making S-2.5d foams, a cap was added on the plastic test tube right after the stirring to allow the pressure to build up inside the tube. The cell structure was studied by scanning electron microscopy (SEM).

Example I-10
Effect of Dehydration Method on Foam Properties

To investigate the effect of alcohol dehydration, two batches of S-1.5d foams were prepared according to the method described above. One batch was dehydrated in absolute alcohol without Voranol and then air dried whereas the other batch was air dried after washing in water without the alcohol dehydration step. These two foams were compared by SEM.

To investigate the effect of wetting agent, S-2.5d foams and S-3h foams were made with and without the presence of Voranol during the alcohol dehydration process. Thq of the two different foams were compared.

Example I-11
Degradation of S-GA Gels and Foams

To characterize the degradation properties of these systems, three S-GA gels (about 200 mg and disk shaped) or foams (about 80 mg) were exposed to pH 1 HCl solution or pH 12.5 NaOH solution at 25° C., 37° C., or 90° C. The pH was maintained by periodically monitoring the pH and adding necessary amounts of either HCl or NaOH. The complete degradation was indicated by the disappearance of the bulk gels or foams. Degradation kinetics of S-2.5d foam and gel in pH 12.5 NaOH solution was studied. The swelling ratio was measured by the sieve method.

Example I-12
Degradation Mechanism

S-2.4d gels were incubated in 6 N HCl and 1 N NaOH solution at 85° C. for 20 hours. The solutions were then filtered, and neutralized. TLC on silica gel (Analtech) was developed (chloroform:methanol=1:1) to examine the degradation mechanism. Sulfuric acid spray agent (Sigma) was used to detect sucrose and its derivatives.

Example I-13
Scanning Electron Microscopy (SEM)

Dried foams were cut to expose their inner structure and then coated by palladium gold alloy in a Hummer I Sputter Coater (Technics, Alexandria, Va.) and analyzed in a JEOL JSM-840 scanning electron microscope. The pore size of the foams was estimated from the SEM images by averaging the diameter of ten cells.

Example I-14
Foam Compressibility Test

The compressibility of foams in the swollen state is an important property for practical applications. To examine the pressure endurance of the foam, a simple method was developed to compare different foams.

7 ml of DDW was added to 300 mg of S-3h, S-1.5d or S-2.5d foam samples in a 20 ml glass beaker (Outer diameter=32 mm, height=40 mm). The breaker was sealed with Parafilm and let stand for 48 hours to reach equilibrium.

An AMES Bench Comparator (Waltham, Mass.) was used for the test. The beaker was fixed to a lab jack with Scotch tape. The self-weight of the spindle was calibrated with a balance to be 10 g. The diameter of the lower touch was 25 mm. The lower touch was aligned to the center of the beaker. Before the test, the foam was pre-pressed to remove air by placing a 200 g weight on the upper touch for 2 minutes. Then the weight was removed to let the foam relax. The process was repeated 2–3 times. Then a 100 g weight was put onto the upper touch (the total weight including the spindle was 110 g). After waiting for about 15 seconds to ensure the spindle did not go any further, the position of the spindle was recorded. Then another 100 g weight was added onto the upper touch to compress the foam more (the total weight was 210 g). After 15 seconds the position was recorded again. The difference between the two positions was the displacement under weight from 110 g to 210 g. This process was repeated by removing and replacing the second 100 g weight 4–5 times. The displacement decreased gradually until it reached a constant value, $\Delta D$. The compression coefficient K was calculated by the formula:

$$K = \Delta W / \Delta D$$

Here $\Delta W$ was 100 g (=210 g–110 g).

II. Hydrophobic Sucrogels and Sucrofoams

Example II-1

Synthesis of Sucrose Methacrylate Acetate (S-MA-A) Monomer

Two batches of S-MA-A monomers were synthesized following reaction (II) shown in FIG. 1. The batch having a higher degree of modification (S-H) was synthesized in a 500 ml three-necked round-bottomed flask equipped with a drying tube and purged with argon gas. Sucrose (4 g) was dissolved in 100 ml anhydrous pyridine at 60° C. over reflux. A small amount of p-methoxyphenol was added as an inhibitor. The flask was cooled down to 0° C. in ice-water. Freshly distilled cold methacrylol chloride (4.6 ml) was added dropwise over a 1-hour period while continuously stirring. The solution was stirred for 2 more hours at 0° C. and 24 more hours at room temperature. After the reaction finished, a small lump of pyridine salt at the flask bottom was removed with a forceps. The solution was cooled down to 0° C. again and 3.5 ml of cold acetyl chloride (98.5%) was added dropwise over 1 hour while continuously stirring. The solution was allowed to reach room temperature and react for 24 hours.

After the reaction, the solution was filtered to remove the pyridine salt and then evaporated to remove the unreacted methacrylol chloride, acetyl chloride, and pyridine. A brown syrup was obtained which was then dissolved in 100 ml chloroform. This solution was washed sequentially with 200 ml of DDW, 100 ml of 0.5 N HCl (twice), 100 ml of 0.5 N NaHCO$_3$ (twice), and 100 ml of DDW (twice) to remove residual pyridine and other water soluble impurities. The solution was then dried over MgSO$_4$, concentrated and vacuum dried to a glassy syrup. On TLC (acetone:chloroform=1:5), a series of spots showed that S-MA-A monomers with different degrees of substitution were synthesized. The monomer mixture was used to make hydrophobic sucrogels and sucrofoams without further purification.

S-MA-A having a lower degree of modification (S-L) was synthesized by the same method except that 1.7 ml of methacrylol chloride and 3.4 ml of acetyl chloride were used. After vacuum drying, a pale brown solid product was obtained.

Example II-2

Characterization of the S-H and S-L Monomers $^1$H NMR spectra were obtained with a Bruker ARX-300 MHz NMR spectrometer using a 15% solution in deuterated chloroform with TMS as an internal standard. In quantitative C-13 NMR measurements, chromium acetylacetonate (a NMR relaxation reagent for quantitative NMR analysis), was also dissolved in the sample to make its final concentration of 0.03 M. The quantitative C-13 NMR analysis was performed at 75 MHz with a 3-second pulse delay time. The gate-decoupled pulse sequence was also employed to suppress the NOE effect.

Fourier transform infrared spectra (FTIR) were obtained on a Nicolet 20SXC FTIR spectrometer using NaCl plates. Sixteen scans were accumulated for each measurement.

Example II-3

Gel Formation

15% S-H monomer in toluene was gelled easily by γ-irradiation of 0.12 Mrad. Gel was also formed chemically at 65° C. in 12 hours when 2,2'-azobis(2-methyl-propionitrile) (AIBN) (Kodak; Rochester, N.Y.) was used as an initiator. When to 1 ml of 20% S-H monomer solution in dimethyl sulfoxide (DMSO) was added 40 μl of 20% APS in DDW and 40 μl of 20% TEMED in DDW, gel was formed within one minute at 60° C.

40% S-L monomer solution in isopropanol was gelled by γ-irradiation of 0.12 Mrad. By chemical initiation, 40 μl of 20% APS in DDW and 40 μl of 20% TEMED in DDW were added to 400 μl of 40% S-L monomer solution. Gel was formed in less than 1 minute at 85° C.

Example II-4

S-MA-A Foam

S-H foam: S-H monomer (final concentration of 20%), Silwet L7605 (OSi Specialties Inc.; Sisterville, W. Va.) (final concentration of 1.2%), Pluronic P105 (BASF) (final concentration of 0.2%) were dissolved in DMSO. 15 mg of APS solid, 50 mg of NaHCO$_3$ and 40 μl of 20% TEMED in DMSO were added to 1 ml of the monomer solution at 60° C. After waiting for 20 seconds, 20 mg of p-toluenesulfonic acid monohydrate (98.5%) was added and stirred vigorously for 2–5 seconds. The foam was then kept at 60° C. for 10 minutes for curing.

S-L foam: S-L monomer was dissolved in isopropanol to make a final concentration of 40%. To 400 μl of this monomer solution were added 50 μl of 5% Pluronic F-127 in DDW, 50 μl of 10% Silwet L-7605 in DMSO, and 35 μl of AA in a glass test tube. The mixture was heated in a water bath for 30 seconds to bring its temperature to 85° C. Then 40 μl of 20% APS in DDW, 40 μl of 20% TEMED in DDW, and 50 mg of NaHCO$_3$ powder were added sequentially. The mixture was stirred to generate a foam which settled within a minute. Foam was allowed to cure for 10 minutes at room temperature. 20 μl of 6 N HCl was also used to replace the AA. Unless specially mentioned, the foams used in the later studies were prepared using AA.

Copolymer foam of S-L and S-2.5d: 4 ml of 40% S-L in isopropanol was mixed with 2 ml of S-2.5d solution (monomer concentration of 18%). To 500 μl of this co-monomer solution were added 40 μl of 5% Pluronic F-127 in DDW, 70 μl of 10% Silwet L7605 in DMSO, and 10 μl of 6 N HCl. The mixture was heated in a water bath for 30 seconds to bring its temperature to 60° C. Then 40 μl of 20% APS in DDW, 40 μl of 20% TEMED in DDW, and 50 mg of NaHCO$_3$ powder were added sequentially. After stirring, the foam was cured at room temperature for 10 minutes.

All of the hydrophobic foams prepared above were washed in DDW and ethanol, then dehydrated and dried as described above for the S-GA foams.

Example II-5
Degradation of the S-L Monomer and Foam

Sucrose, S-L monomer, and S-L foam were incubated in 1 N NaOH and 1 N HCl at 90° C. for 12 hours. TLC on silica gel was developed (chloroform:methanol=1:1) to examine the degradation mechanism.

III. Synthesis of N-methacryloyl Aminocarboxylate Monomers

Example III-1
Synthesis of N-methacryloyl Aminocarboxylic Acids

N-methacryloyl aminocaproic acid and N-methacryloyl leucine were synthesized according to previous methods [Kaczmar, et al. (1976); Kulkarni, et al. (1961)] with slight modification.

A 250 ml round bottom flask equipped with two dropping funnels and a thermometer was charged with 30 ml of deionized distilled water and 0.1 mole of 6-aminocaproic acid or leucine. In the case of leucine, 6 g of sodium hydroxide was added in advance. The mixture was cooled in an ice bath and freshly distilled methacryloyl chloride and concentrated solution of sodium hydroxide (11.4 g of NaOH to 25 ml of deionized distilled water) were added dropwise simultaneously under vigorous stirring. The addition of reagents was completed in 1–2 h. During the addition of reagents the temperature of the reaction mixture was maintained below 20° C. and the pH at 8.5–9.5.

After reaction for 3 hr with constant stirring, the solution was acidified carefully to pH 1–2 with 15% HCl solution and extracted with 150 ml of ethyl acetate three times. The extract was dried with anhydrous magnesium sulfate, and the product was crystallized with benzene and toluene. Crude products were recrystallized with ethyl acetate.

N-methacryloyl-11-aminoundecanoic acid (11-AUA) was synthesized by a previous method [Yeoh, et al. (1989)]. Initially 500 ml of 95% ethanol and 0.1 mole of 11-aminoundecanoic acid was added to a 2 l reactor which was equipped with a dropping funnel and a thermometer. 13.3 g of sodium hydroxide was charged in advance to solubilize 11-AUA and to make the solution basic. While the temperature was kept below 30° C., methacryloyl chloride (15 ml) was added dropwise using a funnel. After the addition of methacryloyl chloride the mixture was stirred for 3 h at room temperature. The mixture was filtered after reaction and then the filtrate was acidified with 10% hydrochloric acid to pH 1–2. The acidified filtrate was titrated with deionized distilled water (4 L) to precipitate N-methacryloyl-11-aminoundecanoic acid. The crude product was recrystallized using aqueous ethanol.

After drying in a vacuum oven for 1 day at room temperature, N-methacryloyl aminocarboxylic acids were used for the subsequent step in the synthesis. The purity of N-methacryloyl aminocarboxylic acids was confirmed by TLC using chloroform:methanol (10:1) mixture. The rf values in TLC and yields for N-methacryloyl-6-aminocaproic acid, N-methacryloyl leucine, and N-methacryloyl-11-aminoundecanoic acid were 0.44 and 55%, 0.46 and 67%, and 0.54 and 48%, respectively.

Example III-2
Synthesis of Sucrose Monomers by Esterifications of Sucrose

Esterifications of sucrose with N-methacryloyl aminocarboxylic acids were carried out using the Mitsunobu reaction. The general procedure of the reaction was adapted from a previous method [Abouhilale et. al. (1991)] with slight modification.

A 500 ml round bottom flask equipped with calcium chloride drying tube and two rubber stoppers was charged with sucrose (1 eq.), adequate volume of anhydrous dimethylformamide (150–200 ml depending on the amount of sucrose), triphenylphosphine (1.7 eq. for N-methacryloyl-6-aminocaproic acid, and 1.2 eq. for N-methacryloyl leucine and N-methacryloyl-11-aminoundecanoic acid) and N-methacryloyl aminocarboxylic acid (1.5 eq.of N-methacryloyl caproic acid, and 1.0 eq. of N-methacryloyl leucine and N-methacryloyl-11-aminoundecanoic acid). After the reaction flask was purged with argon gas, the solution was cooled down to 0° C. in an ice bath, and diisopropyl azodicarboxylate (same amount as triphenyl phosphine) was added dropwise using a dropping funnel. After 30 more minutes in the ice bath, the mixture was left at room temperature for 2–3 days while stirring.

The progress of the reaction was monitored by TLC using chloroform:methanol (3:1) mixture. When the band of sucrose on TLC plate did not decrease further, the mixture was transferred to 1 L of hexane and then chloroform was added to the mixture to precipitate sucrose monomers from the solvent mixture. The crude precipitates were purified further with gradient elutions of chloroform-methanol eluents in the column chromatography. The chloroform:methanol ratios were 8:1, 6:1, and 4:1 for MACS, 10:1, 8:1, and 6:1 for DMACS and MLS, and 15:1, 12:1, and 10:1 for MAUS. TLC of purified products was performed on silica gel plates using chloroform:methanol (3:1) mixture and purified products were visualized by charring with spray agent.

The identities of the sucrose monomers were determined by elemental analysis and by obtaining their $^1$H- and $^{13}$C-NMR spectra using a Bruker ARX 300 spectrometer. The yields of modified sucrose ranged from 9% to 19%. The rf values in TLC: 0.26 for MACS, 0.49 for DMACS, 0.39 for MLS, and 0.42 for MAUS.

Example III-3
Synthesis of Thermoreversible Hydrogels 25 ml of 0.5M MACS, 25 ml of 0.5M MLS, 50 ml of 0.5M PPGM, 50 ml of 0.5M PEGEEM, 10 ml of 0.25M DMACS and 10 ml of 0.25M MAUS solutions were prepared with 50% methanol solution. The structures of monomers used for the hydrogel synthesis are shown in FIG. 7. These solutions were used as stock solutions of sucrose monomers for the preparation of hydrogels. DMACS was used as a crosslinking agent in the synthesis of hydrogels.

Various mixtures of monomer solutions were obtained by changing the volume fraction of each monomer solution. The final volume was 6 ml. 60 μl of 10% ammonium persulfate solution and 60 μl of 10% tetramethylethylenediamine (TEMED) were added to the monomer mixtures to initiate free radical polymerization at room temperature. The final mixture, after shaking for 10 sec, was transferred into a mold to make slab gels with a dimension of 7.5 cm×7.5 cm×0.3 cm. Polymerization was allowed for more than 6h at room temperature. The prepared hydrogels were cut into discs with a diameter of 1.5 cm for the investigation of swelling kinetics, 1.2 cm for degradation studies, and 1.0 cm for SEM observations. Prepared hydrogel discs were washed once with ethanol and several times with cold deionized water. After the last washing, hydrogel discs were equilibrated for more than 1 day at 5° C.

Example III-4
Temperature Dependence of Swelling and Swelling Kinetics of Sucrogels The thermosensitivities of the prepared hydrogels were examined. Each hydrogel disc was placed in a weighing boat which was designed to weigh a fragile swollen hydrogel. The support for hydrogel disc was composed of a copper wire wrapped with a piece of nylon net. Weighing boats were made by fitting the supports into the plastic frames.

Swollen gels previously equilibrated at 5° C. were placed into the bath at 60° C. The volume change of hydrogels was measured using the swelling ratio, which was defined as the weight of a swollen gel divided by the weight of a dried gel. The temperature-dependent swelling kinetics was examined by first swelling the hydrogel to an equilibrium at 60° C. and then changing the temperature to 5° C. To obtain a transition profile of thermosensitive swelling, previously swollen hydrogels were put into the water bath with accurate temperature control. With the increase in temperature, the hydrogel weight was measured at each temperature. Hydrogels were kept at each temperature for 1 day.

Example III-5
Degradation of Thermoreversible Hydrogels

Thermoreversible hydrogels with composition of PPGM:MLS:DMAC=5:4:1 and PPGM:MACS:DMACS=5.00:4.95:0.05 were placed into beakers containing 100 ml of acidic buffer solution (pH 2.0) or basic solution (pH 12.0). Solutions were kept at room temperature during the experiments. Buffer solutions were prepared from Hydrion buffer powders.

Degradation profiles were expressed using the fraction of a remaining hydrogel, which was defined as the weight of a gel divided by the weight of the original swollen gel. The sites of degradation in hydrogels were determined by performing TLC of solutions from the degradation test on silica gel plates. Samples for TLC were retrieved from test solutions which were prepared separately from the above tests before and after degradation. After the development of silica gel plates with methanol:chloroform (1:1) mixture, they were visualized by charring with spray reagent which contained sulfuric acid.

Example III-6
Scanning Electron Microscopic (SEM) Observation

Thermoreversible hydrogels with compositions of PPGM-MLS-DMACS (5:4:1) and PPGM-MACS-DMACS (5.00:4.95:0.05) were swollen in water at 5° C. for 1 day. After treatment of each gel with hot water for 20 sec, 30 min, and 1 day, partially or completely shrunken thermoreversible hydrogels were dropped into liquid nitrogen and then dried by freeze drying. These hydrogels were visualized using a JEOL JSM-840 Scanning Electron Microscope.

Although the present invention has been discussed hereinabove by way of examples for the purpose of illustration and clarity of understanding, it should be appreciated that the scope of the invention is instead defined by the appended claims and equivalents thereof.

REFERENCES

The pertinent disclosures of the references listed below and discussed hereinabove are incorporated herein by reference.

(1) Gruber, H. Hydrophile polymergele mit reaktiven gruppen, I. Herstellung und polymerisation von glucose- und saccharosemethacrylaten; *Monatsh. F. Chem.*, 1981, 112, 273.

(2) Patil, D. R.; Rethwisch, D. R.; Dordick, J. S.; Enzymatic synthesis of a sucrose-containing linear polyester in nearly anhydrous organic media; *Biotechnology and Bioengineering*, 1991, 37, 639.

(3) Garcia-Gonzalez; Kellaway, I. W.; Blanco-Fuente, H.; Anguiano-Igea, S.; Delgado-Charro, B; Otero-Espinar, F. J.; Blanco-Mendez, J; Design and evaluation of buccoadhesive metoclopramide hydrogels composed of poly (acrylic acid) crosslinked with sucrose; *Int'l. J. Pharm.*, 1993, 100, 65.

(4) Lepisto, M.; Artursson, P.; Edman, P.; Laakso, T.; Sjoholm, L.; Determination of the degree of derivatization of acryloylated polysaccharides by fourier transform proton NMR spectroscopy; *Anal. Biochem.*, 1983, 133, 123.

(5) Laakso, T.; Stjarnkvist, P.; Sjoholm, I.; Biodegradable microspheres VI: Lysosomal release of covalently bound antiparasitic drugs from starch microparticles; *J. Pharm. Sci.*, 1987, 76, 134.

(6) Artursson, P; Edman, P; Laakso T.; Sjoholm, I.; Characterization of polyacryl starch microparticles as carriers for proteins and drugs; *J. Pharm. Sci.*, 1984, 73, 1507.

(7) Edman, P.; Ekman, B; Sjoholm, I; Immobilization of proteins in microspheres of biodegradable polyacryldextrans; *J. Pharm. Sci.*, 1980, 69, 838.

(8) Smedt, S. C. D.; Lauwers, A.; Demeester, J.; Steenbergen, M. J. V.; Hennink, W. E.; Foefs S. P. F. M.; Characterization of the network structure of dextran glycidyl methacrylate hydrogels by studying the rheological and swelling behavior; *Macromolecules*, 1995, 28, 5082.

(9) Park, K.; Enzyme-digestible swelling hydrogels as platforms for long-term oral drug delivery: Synthesis and characterization; *Biomaterials*, 1988, 9, 435.

(10) Shalaby, W. S. W.; Park, K.; Biochemical and mechanical characterization of enzyme-digestible hydrogels; *Pharmaceutical Research*, 1990, 7, 816.

(11) Starks, C. M.; Phase transfer catalysis. I. Heterogeneous reaction involving anion transfer by quaternary ammonium and phosphonium salts; *JACS*, 1971, 93, 195.

(12) Hoppe, H.; Koppe, J.; Winkler, F.; Improved method for determining acrylamide in polyacrylamide; *Plaste Kautsch*, 1977, 24, 105.

(13) Akoh, C. C.; Swanson, B. G.; One-stage synthesis of raffinoise fatty acid polyesters; *J. Food Sci.*, 1987, 52, 1570.

(14) Akoh, D. C.; Swanson, B. G.; Synthesis and properties of alkyl glycoside and starchyose fatty acid polyesters; *J. Am. Oil Chem. Soc.*, 1989, 66, 1295.

(15) Wehrli, F. W. and Wirthlin, T. *Interpretation of C-13 NMR spectra*, Heyden and Sons Inc.; New York, N.Y., 1976, 225.

(16) Shalaby, W. S. W.; Blevins, W. E.; Park, K.; In vitro and in vivo studies of enzyme-digestible hydrogels for oral drug delivery; *Journal of Controlled Release*, 1992, 19, 131.

(17) Kellenberger, S. R. et al. U.S. Pat. No. 5,149,335.

(18) Huglin, M; Zakaria, M., Observations on the homogeneity of crosslinked copolymers prepared by γ-irradiation; *Polymer*, 1984, 25, 797.

(19) Davis, T; Huglin, M.; Some mechanical properties of poly(2-hydroxyethyl methacrylate) gels swollen in water/ 1,4-dioxane mixtures; *Makromol Chem. Rapid Commun.*, 1988, 9, 39.

(20) Garcia, O; Trigo, R. M.; Blanco, M. D.; Teijon, J. M.; Influence of degree of crosslinking on 5-fluorouracil release from poly(2-hydroxyethyl methacrylate) hydrogels; *Biomaterials*, 1994, 15, 689.

(21) Jin, X.; Carfagna, C; Nicolais, L.; Lanzetta. R.; Synthesis, characterization, and in vitro degradation of a novel thermotropic ternary copolyester based on p-hydroxybenzoic acid, glycolic acid, and p-hydroxycinnamic acid; *Macromolecules,* 1995, 28, 4785.

(22) Dubrovskii, S. A.; Afanaseva, M. V.; Lagutina, M. A.; Kazanskii, K. S.; Measurement of swelling in weakly crosslinked hydrogels; *Polymer Science U.S.S.R.,* 1990, 32, 166.

(23) Hartley, F. D.; Cross, M. M.; Lord, F. W.; The mechanism of polyurethane foam formation; In *Advances in Polyurethane Technology;* J. M. Buist and H. Gudgeon, Eds,; John Wiley and Sons Inc.; New York, N.Y., 1968, 139.

(24) Tomlinson, E.; Burger, J. J.; Incorporation of water-soluble drugs in albumin microspheres; In *Methods in Enzymology;* K. J. Widder and R. Green, Eds.; Academic press, Inc.; 1985, 112, 35.

(25) Straathof, A. J. J.; Vrijenhoef, J. P.; Sprangers, E. P. A. T.; Bekkum, H. V; Kieboom, A. P. G.; Enzymic formation of β-D-fructofuranosides from sucrose: activity and selectivity of invertase in mixtures of water and alcohol; *J. Carbohydrate Chemistry,* 1988, 7, 223.

(26) Hickmott, P. W.; Reaction of αβ-unsaturated acid chlorides with alcohols in the presence of tertiary amines; *J. Chem. Soc.,* 1964, 883.

(27) Strumia, M. C.; Zamora, M. N.; Bertorello, H. E.; Hydrogels from acrylic sucrose. Synthesis and characterization; *J. Appl. Poly. Sci.,* Applied Polymer Symposium 49, 9–14, (1991).

(28) Jeong, S. Y.; Kim, S. W.; Eenink, M. J. D.; Feijen, J. Self-regulating insulin delivery systems. I. Synthesis and characterization of glycosylated insulin; *J. Cont. Rel.,* (1984) 1, 57.

(29) Horbett, T. A.; Ratner, B. D.; Kost, J.; Singh, M. *A bioresponsive membrane for insulin delivery;* Plenum Press: New York, (1984) 209.

(30) Yoshida, R.; Sakai, K.; Okano, T.; Sakurai, Y. Pulsatile drug delivery systems using hydrogels; *Adv. Drug Delivery Reviews* (1993) 11, 85.

(31) Hoffman, A. S., Afrassiabi, A. and Dong, L. C., Thermally reversible hydrogels: II. Delivery and selective removal of substances from aqueous solutions., *J. Cont. Rel.,* (1986) 4, 213–222.

(32) Dong, L. C. and Hoffman, A. S., Thermally reversible hydrogels: III. Immobilization of enzymes for feedback reaction control, *J. Cont. Rel.,* (1986) 4, 223–227.

(33) Shalaby, S. W. Thermoreversible gels; In *Water-solution polymers; Synthesis, solution properties, and applications;* S. W. Shalaby, C. L. McCormick and G. B. Butler, Eds.; American Chemical Society; Washington D.C., (1991) 467, 502.

(34) Bae, Y. H., Okano, T. and Kim, S. W., *Makromolek. Chem., Rapid Commun.,* (1988) 9, 185.

(35) Yoshida, M., Asano, M. and Kumakura, M., A new temperature-sensitive hydrogel with α-amino acid group as side chain of polymer., *Eur. Polym. J.,* (1989) 25, 1197–1202.

(36) Yoshida, M., Suzuki, Y., Tamada, M., Kumakura, M. and Katakai, R., External stimulus-responsive poly (methacryloyldipeptides) having sequences of L-amino acyl-L-alanine ethyl esters as pendent groups., *Eur. Polym. J.* (1991) 27, 493–499.

(37) Bae, Y. H., Okano, T., Hsu, R. and Kim, S. W., *Makromolek. Chem., Rapid Commun.,* (1987) 8, 481.

(38) Kulkarni, R. K. and Morawetz., H., Effect of asymmetric centers on free radical polymerization and the properties of polymers: methacrylyl alanine, methacrylyl glutamic acid, acrylyl glutamic acid and their polymers., *J. Polym. Sci.,* (1961) 54, 491–503.

(39) Kaczmar, B. U. and Traser, S., Schlangenkafig-Polymere, 1. Darstellung verschiedener Schlangenkafig-polyelektrolyte auf der Basis von Polyacrylamiden und einem Anionenaustauscher., *Makromol. Chem.,* (1976) 177, 1981–1989.

(40) Yeoh, K. W., Chew, C. H., Gan, L. M. and Koh, L. L., Synthesis and polymerization of surface-active sodium acrylamidoundecanoate., *J. Macromol. Sci.-Chem.,* (1989) A26, 663–680.

(41) Abouhilale, S., Greiner, J. and Riess, J. G., One-step preparation of 6-perfluoroalkylalkanoates of trehalose and sucrose for biomedical uses., *Carbohydrate Research* (1991) 212, 55–64.

(42) Jansson, P.-E., Kenne, L. and Schweda, E., Nuclear magnetic resonance and conformational studies on monoacetylated methyl D-gluco- and D-galacto-pyranosides., *J. Chem. Soc. Perkin Trans.,* (1987) 1, 377–383.

What is claimed is:

1. A gel or foam formed by polymerizing a saccharide having a formula selected from formulas (I)–(VII) as follows:

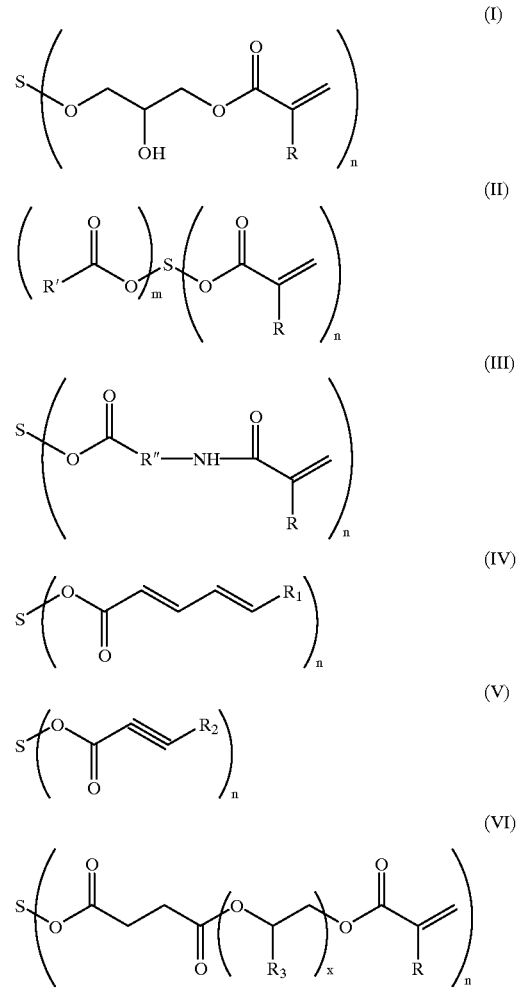

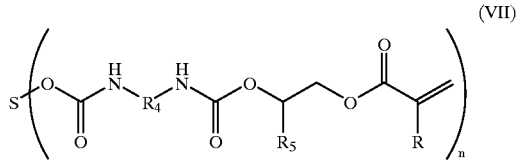

(VII)

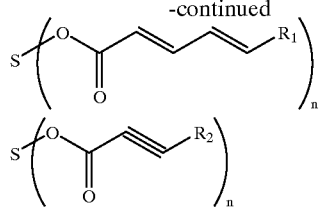

(IV)

(V)

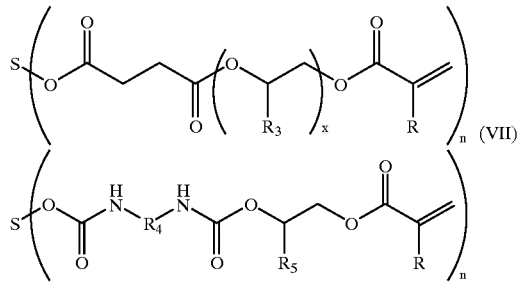

(VI)

(VII)

where S is a saccharide residue, R is hydrogen or a lower alkyl group, and n is an integer from 1 to 8; R' is an alkyl, aryl or alkaryl group, and m is an integer from 0 to 7; R" is an alkylene, arylene, or alkarylene diradical; $R_1$ is a lower alkyl group; $R_2$ is a lower alkyl group; $R_3$ is hydrogen or methyl, and x is an integer from 1 to 10,000; $R_4$ is an alkylene, arylene, or alkarylene diradical, and $R_5$ is hydrogen or lower alkyl.

2. A hydrophilic gel formed by polymerizing a saccharide monomer having formula (I) in claim 1.

3. A hydrophobic gel formed by polymerizing a saccharide monomer having formula (II) in claim 1.

4. A thermoreversible gel formed by polymerizing a saccharide monomer having formula (III) in claim 1.

5. A thermoreversible gel formed by polymerizing a saccharide monomer having formula (III) in claim 1 in the presence of a poly(alkyleneoxide) (meth)acrylate monomer.

6. A thermoreversible gel formed by polymerizing a saccharide monomer having formula (III) in claim 1 in the presence of a crosslinking agent.

7. A hydrophobic gel formed by polymerizing a saccharide monomer having formula (IV) in claim 1.

8. A hydrophobic gel formed by polymerizing a saccharide monomer having formula (V) in claim 1.

9. A hydrophilic gel formed by polymerizing a saccharide monomer having formula (VI) in claim 1.

10. A hydrophilic gel formed by polymerizing a saccharide monomer having formula (VII) in claim 1.

11. A foam prepared by polymerizing a saccharide monomer as in claim 1 in the presence of a blowing agent.

12. A foam prepared by dehydrating the foam of claim 11 with an organic solvent.

13. A foam prepared by dehydrating the foam of claim 11 by freeze-drying.

14. A method of forming a gel or foam comprising the steps of (A) forming a saccharide monomer having a formula selected from formulas (I)–(VII) as follows:

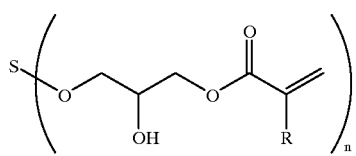

(I)

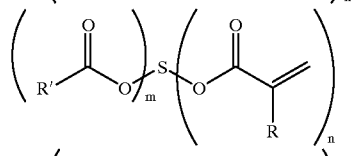

(II)

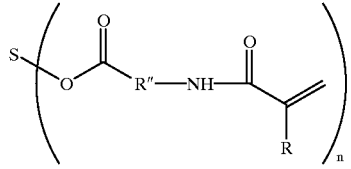

(III)

where S is a saccharide residue, R is hydrogen or a lower alkyl group, and n is an integer from 1 to 8; R' is an alkyl, aryl or alkaryl group, and m is an integer from 0 to 7; R" is an alkylene, arylene, or alkarylene diradical; $R_1$ is a lower alkyl group; $R_2$ is a lower alkyl group; $R_3$ is hydrogen or methyl, and x is an integer from 1 to 10,000; $R_4$ is an alkylene, arylene, or alkarylene diradical, and $R_5$ is hydrogen or lower alkyl; and (B) polymerizing said saccharide to form said gel or foam.

15. The method of claim 14 wherein the polymerization step is accomplished by using mass polymerization, solution polymerization, suspension polymerization, emulsion polymerization, or radiation polymerization.

16. The method of claim 14 wherein said polymerizing step is accomplished by γ-radiation.

17. The method of claim 14 wherein said polymerizing step is by solution polymerization.

18. The method of claim 17 wherein said polymerizing step is in the presence of a polymerization initiator.

19. The method of claim 14 wherein a hydrophilic gel is formed from said saccharaide monomer having formula (I).

20. The method as in claims 16 or 17 wherein said saccharide monomer is sucrose acrylate or sucrose methacrylate acetate.

21. The method of claim 14 wherein a hydrophobic gel is formed from said saccharide monomer having formula (II).

22. The method of claim 14 wherein a thermoreversible gel is formed by polymerizing said sucrose monomer having formula (III) in the presence of a poly(alkyleneoxide) (meth) acrylate monomer.

23. The method of claim 22 wherein the poly (alkyleneoxide) (meth)acrylate monomer is poly (propyleneglycol)methacrylate or poly(ethylene glycol) ethylether methacrylate.

24. The method of claim 14 wherein said polymerizing is conducted in the presence of a crosslinking agent.

25. The method of claim 14 wherein a hydrophobic gel is formed from said saccharide monomer having formula (IV).

26. The method of claim 14 wherein a hydrophobic gel is formed from said saccharide monomer having formula (V).

27. The method of claim 14 wherein a hydrophilic gel is formed from said saccharaide monomer having formula (VI).

28. The method of claim 14 wherein a hydrophilic gel is formed from said saccharaide monomer having formula (VII).

29. The method of claim 14 wherein said polymerizing step is conducted in the presence of a blowing agent to form a foam.

30. The method of claim 29 which includes an additional step following step (B) of dehydrating the foam with an organic solvent.

31. The method of claim 30 wherein said organic solvent is an alcohol.

32. A method of forming a hydrophilic gel comprising polymerizing a saccharide monomer having formula (I):

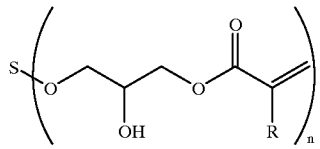

(I)

where S is a saccharide residue, R is hydrogen or a lower alkyl group, and n is an integer from 1 to 8.

33. A method of forming a hydrophobic gel comprising polymerizing a saccharide monomer having formula (II):

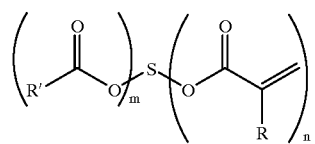

(II)

where S is a saccharide residue, R is hydrogen or a lower alkyl group, R' is an alkyl, aryl, or alkaryl group, n is an integer from 1 to 8, and m is an integer from 0 to 7.

34. A method of forming a thermoreversible gel comprising polymerizing a saccharide monomer having formula (III):

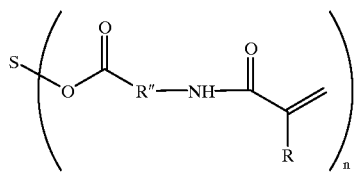

(III)

where S is a saccharide residue, R is hydrogen or a lower alkyl group, R" is an alkylene, arylene, or alkarylene diradical, and n is an integer from 1 to 8.

35. The method of claim 34, wherein said polymerizing is conducted in the presence of a poly(alkyleneoxide) (meth) acrylate monomer.

36. The method of claim 34 in which the poly (alkyleneoxide) (meth)acrylate monomer is poly(propylene glycol)methacrylate or poly(ethylene glycol)ethylether methacrylate.

37. The method of claim 34, wherein said polymerizing is conducted in the presence of a crosslinking agent.

38. A method of forming a hydrophobic gel comprising polymerizing a saccharide monomer having formula (IV):

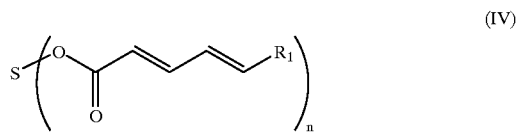

(IV)

where S is a saccharide residue, $R_1$ is hydrogen or a lower alkyl group, and n is an integer from 1 to 8.

39. A method of forming a hydrophobic gel comprising polymerizing a saccharide monomer having formula (V):

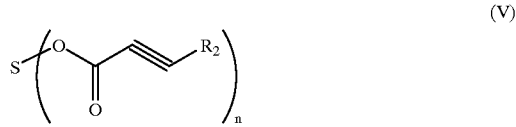

(V)

where S is a saccharide residue, $R_2$ is hydrogen or a lower alkyl group, and n is an integer from 1 to 8.

40. A method of forming a hydrophilic gel comprising polymerizing a saccharide monomer having formula (VI):

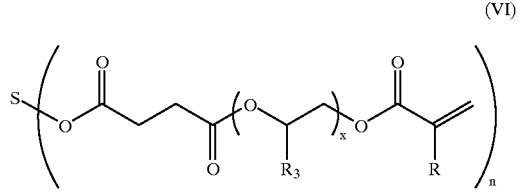

(VI)

where S is a saccharide residue, R is hydrogen or lower alkyl, $R_3$ is hydrogen or lower alkyl, n is an integer from 1 to 8, and x is an integer from 1 to 10,000.

41. A method of forming a hydrophilic gel comprising polymerizing a saccharide monomer having formula (VII):

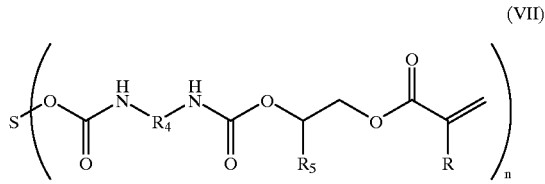

(VII)

where S is a saccharide residue, R is hydrogen or lower alkyl, $R_4$ is an alkylene, arylene, or alkarylene diradical, $R_5$ is hydrogen or lower alkyl, and n is an integer from 1 to 8.

* * * * *

UNITED STATES PATENT AND TRADEMARK OFFICE
CERTIFICATE OF CORRECTION

PATENT NO. : 6,018,033
DATED : January 25, 2000
INVENTOR(S) : Jun Chen, et. al.

It is certified that error appears in the above-identified patent and that said Letters Patent is hereby corrected as shown below:

On the Title page:

Section [54], line three of the Title, change "FORMS" to --FOAMS--.

In the Specification:

Column 4, Line 18, change "Fig. 1 illustrates" to --Figs. 1(A)-1(G) illustrate--.

Figure 4A:
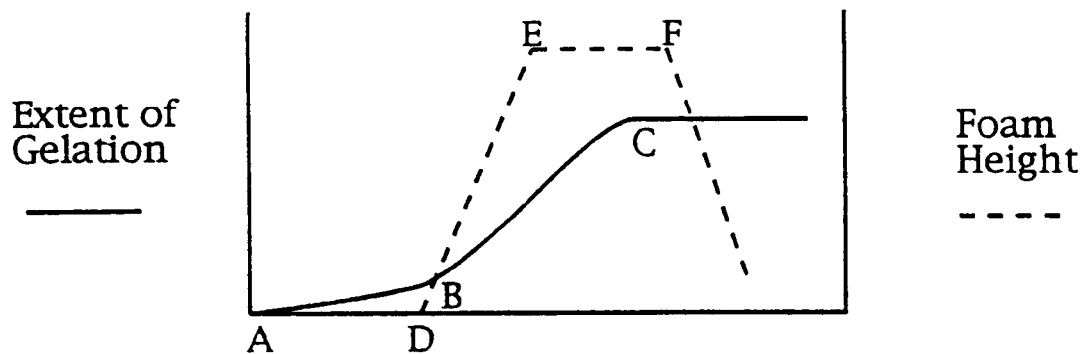
FIG. 4 illustrates the kinetics of various processes: Curve A-B-C describes the polymerization kinetic; A-B indicates the slow polymerization process in the absence of $NaHCO_3$; B-C represents the fast polymerization after the addition of $NaHCO_3$; the plateau after C shows the polymerization is completed; curve D-E-F describes the foaming curve with $NaHCO_3$ being added at point D; D-E is the foam rising phase; E-F represents the foam stabilizing phase; after point F, foam subsides rapidly.
Figure 4B:
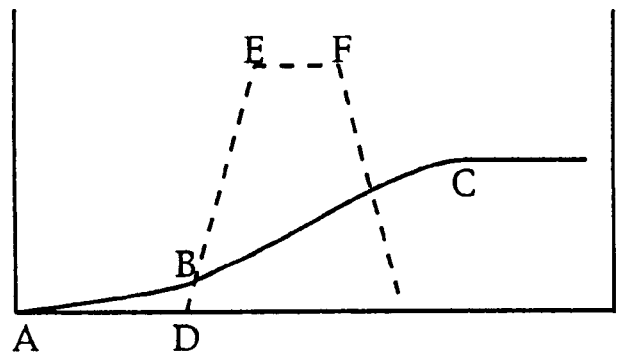
Figure 4C:
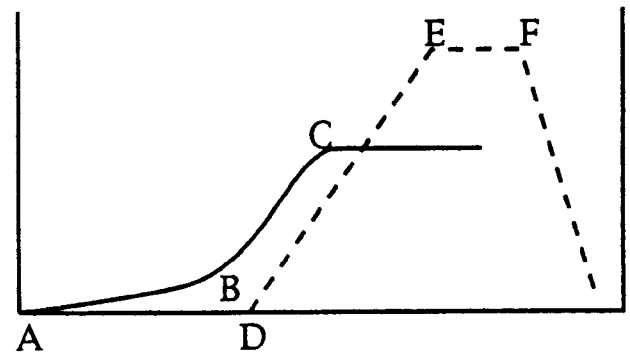

Line 25, change "Fig. 4 illustrates" to --Figs. 4(A)-4(C) illustrate--.

Line 43, change "Fig. 7 illustrates" to --Figs. 7(A)-7(C) illustrate--.

Figure 12A:
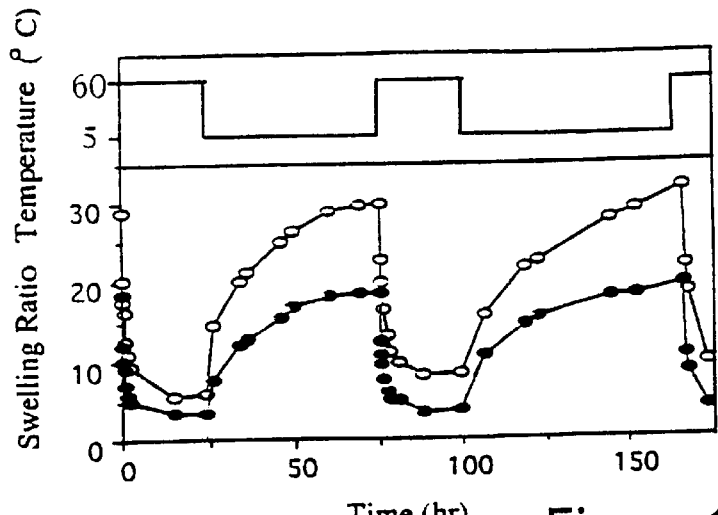
FIG. 12 depicts the thermoreversible swelling and shrinking of sucrogels; (A), sucrogels were made of MACS-PPGM copolymer with the molar ratio of 2:3 and the concentration of DMAC was either 0.5 mole % (○) or 5.0 mole % (●); (B), MACS-PEGEEM (○) and MAUS-PEGEEM (●) sucrogels with the molar ratio of 1:1; (C), MLS-PPGM (○) and MLS-PEGEEM (●) sucrogels with the molar ratio of 1:1. DMACS was used as a crosslinking agent.
Figure 12B:
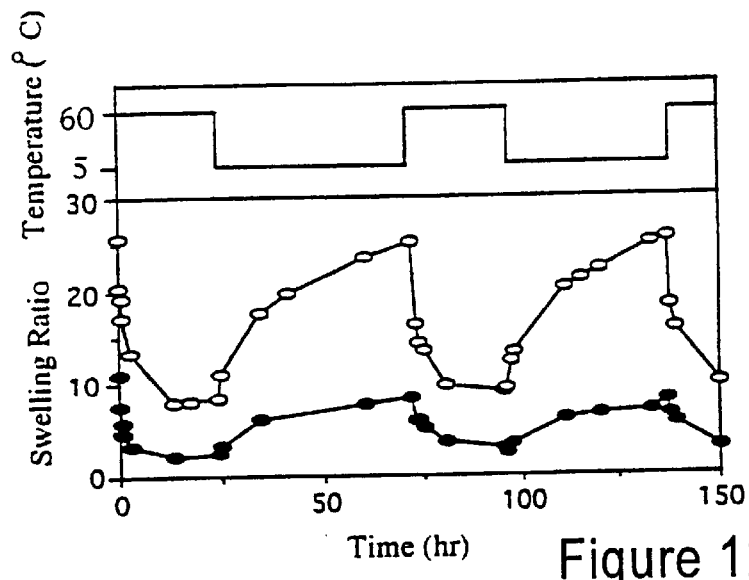
Figure 12C:
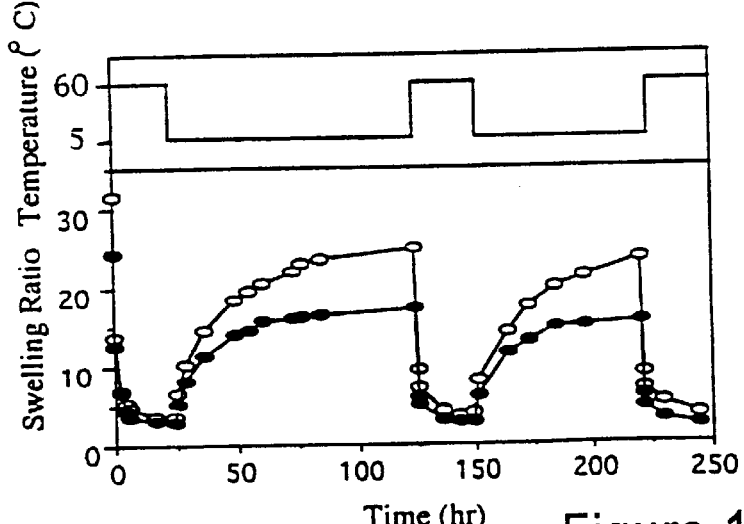

Column 5, Line 1, change "Fig. 12 depicts" to --Figs. 12(A)-12(C) depict--.

Figure 13A:
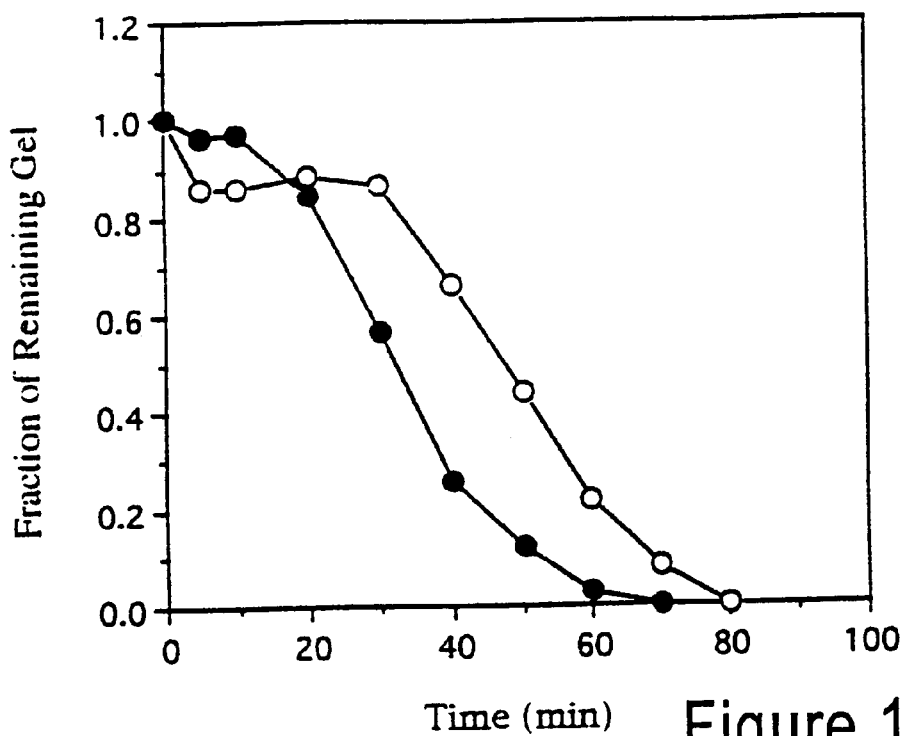
FIG. 13 depicts the degradation of sucrogels; (A), in basic solution (pH 12.0); (B), in acidic solution (pH 2.0). The sucrogels were made of MACS-PPGM (●) and MLS-PPGM (○) copolymers. The molar ratio of monomers was 1:1 and the sucrogels were formed using DMACS as a crosslinking agent.
Figure 13B:
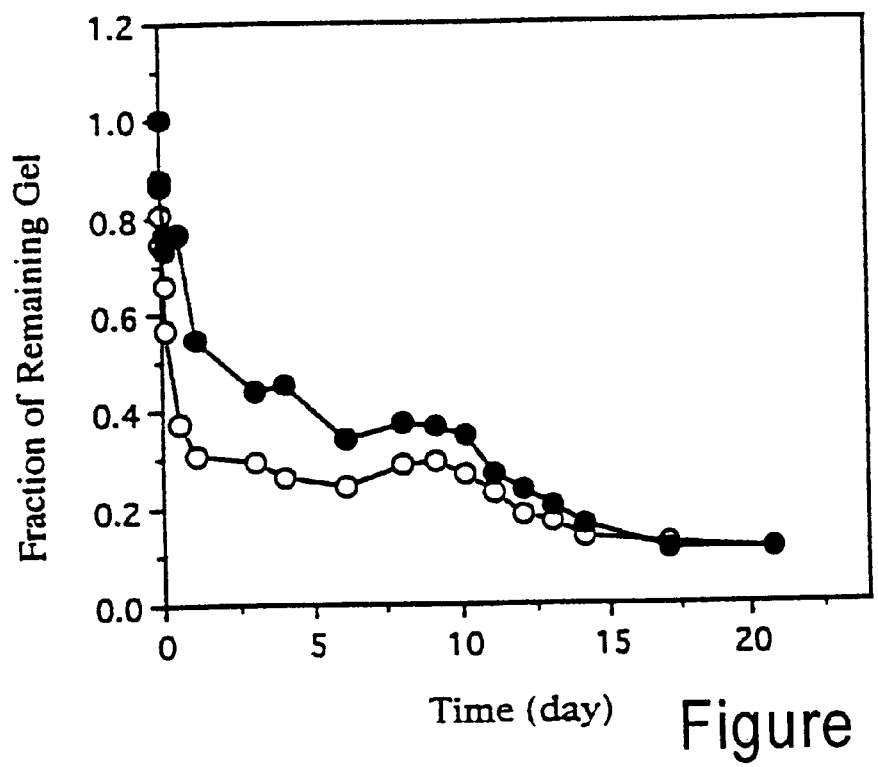

Line 12, change "Fig. 13 depicts" to --Figs. 13(A) and 13(B) depict--.

Signed and Sealed this

Eighth Day of May, 2001

Attest:

NICHOLAS P. GODICI

Attesting Officer       Acting Director of the United States Patent and Trademark Office